US008460868B2

(12) United States Patent (10) Patent No.: US 8,460,868 B2
Brennan (45) Date of Patent: Jun. 11, 2013

(54) GENETIC MARKERS FOR SCHIZOPHRENIA AND BIPOLAR DISORDER

(75) Inventor: Mark David Brennan, Jeffersonville, IN (US)

(73) Assignee: SureGene LLC, Louisville, KY (US)

( * ) Notice: Subject to any disclaimer, the term of this patent is extended or adjusted under 35 U.S.C. 154(b) by 5 days.

(21) Appl. No.: 12/523,243

(22) PCT Filed: Dec. 22, 2008

(86) PCT No.: PCT/US2008/088061
§ 371 (c)(1),
(2), (4) Date: Feb. 4, 2010

(87) PCT Pub. No.: WO2009/082743
PCT Pub. Date: Jul. 2, 2009

(65) Prior Publication Data
US 2010/0151461 A1 Jun. 17, 2010

Related U.S. Application Data

(60) Provisional application No. 61/016,563, filed on Dec. 24, 2007.

(51) Int. Cl.
*C12Q 1/68* (2006.01)
*C12P 19/34* (2006.01)

(52) U.S. Cl.
USPC .......................................... 435/6.1; 435/91.2

(58) Field of Classification Search
None
See application file for complete search history.

(56) References Cited

U.S. PATENT DOCUMENTS

| 5,474,796 A * | 12/1995 | Brennan .................... 427/2.13 |
| 5,800,998 A | 9/1998 | Glucksmann |
| 2003/0108938 A1 | 6/2003 | Pickar et al. |
| 2005/0209181 A1 | 9/2005 | Akil et al. |
| 2006/0177851 A1 | 8/2006 | Brennan et al. |

FOREIGN PATENT DOCUMENTS

| EP | 1266906 A1 | 12/2002 |
| WO | WO0100882 A1 | 1/2001 |
| WO | WO2004051222 A2 | 6/2004 |
| WO | WO2007100913 A2 | 9/2007 |
| WO | WO2007145992 A2 | 12/2007 |
| WO | WO 2009/008896 | 1/2009 |

OTHER PUBLICATIONS

Mummidi et al (Journal of Biological Chemistry 2000 vol. 275 No. 25 pp. 18946-1896).*
Bernstein et al., "Brain region-specific changes in the expression of calcium sensor proteins after repeated applications of ketamine to rats," Neuroscience Letters, 339(2):95-98 (2003).
Bernstein et al., "Increased number of nitric oxide synthase immunoreactive Purkinje cells and dentate nucleus neurons in schizophrenia," Journal of Neurocytology, 30(8):661-670 (2001).
Cichon et al., "Pharmacogenetics of schizophrenia," American Journal of Medical Genetics, 97(1):98-106 (2000).
Database Genecards [Online] "HPCAL 1, Hippocalcin-Like 1," retrieved from http://www.genecards.org/cgi-bin/carddisp.PL?Gene=hpcal1&search=hpcal1&SNP=751#SNP, Updated Jan. 27, 2009.
Database Genecards [Online] "SV2C synaptic vesicle glycoprotein 2C" retrieved from http://www.genecards.org/cgi-bin/carddisp.PL?Gene=SV2C&search=SV2c&SNP=1499#SNP, Updated Jul. 2, 2009.
Freudenberg-Hua et al., "Systematic investigation of genetic variability in 111 human genes-implications for studying variable drug response," The Pharmacogenomics Journal, 5(3):183-192 (2005).
Marcheco-Teruel et al., "A genome-wide linkage search for bipolar disorder susceptibility loci in a large and complex pedigree from the eastern part of Cuba," American Journal of Medical Genetics, Part B, Neuropsychiatric Genetics: The Official Publication of the International Society of Psychiatric Genetics, 141B(8):833-843 (2006).
Sherrington et al., "Localization of a susceptibility locus for schizophrenia on chromosome 5," Nature, 336 (6195):164-167 (1988).
Stober et al., "Association study of 5'-UTR polymorphisms of the human dopamine transporter gene with manic depression," Bipolar Disorders, 8(5 Pt1):490-495 (2006).
Zhang et al., "Dopamine transporter polymorphisms and risperidone response in Chinese schizophrenia patients: an association study," Pharmacogenomics, 8(10):1337-1345 (2007).
International Search Report issued on Sep. 30, 2009 in PCT/US2008/088061.
Bennett et al., "The Wellcome trust UK-Irish bipolar affective disorder sibling-pair genome screen: first stage report," Mol. Psychiatry, 7:189-200 (2002).
Braunewell et al., "Abnormal Localization of Two Neuronal Calcium Sensor Proteins, visinin-Like Proteins (VILIPs)-1 and -3, in Neocortical Brain Areas of Alzheimer Disease Patients," Demantia and Geriatric Cognitive Disorders, vol. 12, pp. 110-116 (2001).
Clayton, "A Generalization of the Transmission/D sequilibrium Test for Uncertain-Haplotype Transmission," Am. J. Hum. Genet., vol. 65, pp. 1170-1177 (1999).
Cloninger et al., "Genome-Wide Search for Schizophrenia Suceptibility Loci: The NIMH Genetics Initiative and Millennium Consortium," American Journal of Medical Genetics, vol. 81 pp. 275-281 (1998).
Davis et al., "Statistical Approaches to Effectiveness Measurement and Outcome-Driven Re-Randomizations in the Clinical Antipsychotic Trials of Intervention Effectiveness (CATIE) Studies," Schizophrenia Bulletin, vol. 29, pp. 73-80 (2003).
Devlin et al., "Genome-wide multipoint linkage analyses of multiplex schizophrenia pedigree from the oceanic nation of Palau," Molecular Psychiatry, vol. 7, pp. 689-694 (2002).
Faraone et al., "Genome Scan of European-American Schizophrenia Pedigrees: Results of the NIMH Genetics Iniative and Millennium Consortium," American Journal of Medical Genetics, vol. 81, pp. 290-295 (1998).
Harrison and Owen, "Genes for Schizophrenia? Recent findings and their pathophysiological implications," Lancet, vol. 361(9355): pp. 417-419 (2003).
Hong et al., "Genetic Mapping Using Haplotype and Model-Free Linkage Analysis Supports Previous Evidence for a Locus Predisposing to Severe Bipolar Disorder at 5q31-33," American Journal of Medical Genetics Part B, vol. 125B, pp. 83-86 (2004).

(Continued)

*Primary Examiner* — Katherine Salmon
(74) *Attorney, Agent, or Firm* — Fish & Richardson P.C.

(57) ABSTRACT

The invention provides haplotypes and SNPs of the HPCAL1 and SV2C genes which predict the risk for developing schizophrenia or bipolar disorder and predict which patients are likely to respond to a given treatment or are more likely to experience negative side effects.

12 Claims, No Drawings

OTHER PUBLICATIONS

Janz et al., SV2C is a Synaptic Vesicle Protein with an Unusually Restricted Localization: Anatomy of a Synaptic Vesicle Protein Family, Neuroscience, vol. 94, pp. 1279-1290 (1999).

Kauffmann et al., "NIMH Genetics Iniative Millennium Schizophrenia Consortium: Linkage Analysis of African-American Pedigrees," American Journal of Medical Genetics, vol. 81, pp. 282-289 (1998).

Kendler et al., "Clinical Features of Schizophrenia and Linkage to Chromosomes 5q, 6p, 8p, and 10p in the Irish Study of High-Density Schizophrenia Families," Am. J. Psychiatry, vol. 157, pp. 402-408 (2000).

Laird and Lange, "Family-based designs in the age of large-scale gene-association studies," Nature Reviews/Genetics, vol. 7, pp. 385-394 (2006).

Lazzell et al., "SV2B Regulates Synaptotagmin 1 by Direct Interaction," The Journal of Biological Chemistry, vol. 279, pp. 52124-52131 (2004).

Lewis et. al., "Genome Scan Meta-Analysis of Schizophrenia and Bipolar Disorder, Part II: Schizophrenia," Am. J. Hum. Genet, vol. 73, pp. 34-48 (2003).

Lieberman et al., "Effectiveness of Antipsychotic Drugs in Patients with Chronic Schizophrenia," The New England Journal of Medicine, vol. 353, pp. 1209-1223 (2005).

Martin et al., "Accounting for Linkage in Family-Based Tests of Association with Missing Parental Genotypes," Am. J. Hum. Genet., vol. 73, pp. 1016-1026 (2003).

Middleton et al., "Genomewide linkage analysis of bipolar disorder by use of a high-density single-nucleotide-polymorphism (SNP) genotyping assay: a comparison with microsatellite marker assays and finding of significant linkage to chromosome 6q22," Am. J. Hum. Genet. 74:886-897 (2004).

Park et al., "Linkage analysis of psychosis in bipolar pedigrees suggests novel putative loci for bipolar disorder and shared susceptibility with schizophrenia," Molecular Psychiatry, vol. 9, pp. 1091-1099 (2004).

Schivell et al., "SV2A and SV2C contain a unique synaptotagmin-binding site," Molecular and Cellular Neuroscience, vol. 29, pp. 56-64 (2005).

Shink et al., "Support for the presence of bipolar disorder susceptibility loci on chromosome 5: Heterogentity in a homogeneous population in Quebec," Progress in Neuro-psychophmaracology & Biological Psychiatry, vol. 26, pp. 1273-1277 (2002).

Straub et al., "Genome-wide scans of three independent sets of 90 Irish multiplex xchizophrenia families and follow0up of selected regions in all families provides evidence for multiple susceptibility genes," Molecular Psychiatry, vol. 7, pp. 542-559 (2002).

Stroup et al., "The National Institute of Mental Health Clinical Antipsychotic Trials of Intenrvention Effectiveness (CATIE) Project: Schizophrenia Trial Design and Protocol Development," Schizophrenia Bulletin, vol. 29, pp. 15-31 (2003).

Sullivan et al., "Genomewide association for schizophrenia in the CATIE study: results of stage 1," Molecular Psychiatry, vol. 13, pp. 570-584 (2008).

Williams et al., "A two-stage genome scan for schizophrenia susceptibility genes in 196 affected sibling pairs," Hum. Mol. Genet. 8:1729-1739 (1999).

Xu et al., "SV2 modulates the size of the readily releasable pool of secretory vesicles," Nature Cell Biology, vol. 3, pp. 691-698 (2001).

* cited by examiner

GENETIC MARKERS FOR SCHIZOPHRENIA AND BIPOLAR DISORDER

CROSS-REFERENCE TO RELATED APPLICATIONS

This application is the U.S. National Stage under 35 USC §371 of International Application Number PCT/US2008/088061, filed on Dec. 22, 2008, which claims the benefit of U.S. Provisional Patent Application Ser. No. 61/016,563, filed on Dec. 24, 2007; the entire contents of the foregoing are hereby incorporated by reference.

CLAIM OF PRIORITY

This application claims the benefit of U.S. Provisional Patent Application Ser. No. 61/016,563, filed on Dec. 24, 2007, the entire contents of which are hereby incorporated by reference.

FEDERALLY SPONSORED RESEARCH OR DEVELOPMENT

This invention was made with Government support under Grant Nos. R43 MH078437, N01 MH900001, and MH074027, awarded by the National Institutes of Health. The Government has certain rights in the invention.

ACKNOWLEDGEMENT

This invention was made with an award from the Kentucky Cabinet for Economic Development, Department of Commercialization and Innovation, under Grant Agreement KSTC-184-512-07-007 with the Kentucky Science and Technology Corporation.

TECHNICAL FIELD

This invention relates to genetic markers of schizophrenia (SZ) and/or Bipolar Disorder (BD) and methods of use thereof.

BACKGROUND

Schizophrenia (SZ) and bipolar disorder (BD) are severe and persistent debilitating psychiatric illnesses that are generally associated with considerable morbidity and extreme disability. Due to the severity of these disorders, especially the negative impact of a psychotic episode on a patient, and the diminishing recovery after each psychotic episode, there is a need to more conclusively identify individuals who have or are at risk of developing SZ or BD, for example, to confirm clinical diagnoses, to allow for prophylactic therapies, to determine appropriate therapies based on their genotypic subtype, and to provide genetic counseling for prospective parents with a history of the disorder.

Various genes and chromosomes have been implicated in etiology of SZ and BD. For example, whole genome scans for genes involved in SZ and BD have implicated chromosome 2 (see, e.g., Williams et al., Hum. Mol. Genet. 8:1729-1739 (1999); Middleton et al., Am. J. Hum. Genet. 74:886-897 (2004); Bennett et al., Mol. Psychiatry 7:189-200 (2002)).

Similarly, whole genome scans for genes involved in SZ and BD have implicated chromosome 5, but these linkage scans have generally been too low in resolution to identify specific genes (see, e.g., Park et al., Mol. Psychiatry 9:1091-1099 (2004); Kendler et al., Am. J. Psychiatry 157:402-408 (2000); Straub et al., Mol. Psychiatry 7:542-559 (2002); Devlin et al., Mol. Psychiatry 7:689-694 (2002); Lewis et al., Am. J. Hum. Genet. 73:34-48 (2003); Hong et al., Am. J. Med. Genet. B Neuropsychiatr. Genet. 125:83-86 (2004); Marcheco-Teruel et al., Am. J. Med. Genet. B Neuropsychiatr. Genet. 141:833-843 (2006); Shink et al., Prog. Neuropsychopharmacol. Biol. Psychiatry 26:1273-1277 (2002).

SUMMARY

Single nucleotide polymorphism (SNP) markers in a number of genes (including hippocalcin-like 1 gene (HPCAL1), and glycoprotein 2C gene (SV2C) were used to evaluate samples from the NIMH Schizophrenia Genetics Initiative. Based on the results, associations of each of these genes with schizophrenia and bipolar disorder and clinical parameters of these diseases were identified. Thus, the invention includes methods of determining risk of developing schizophrenia (SZ) and bipolar disorder (BD), of identifying individuals more likely to display particular clinical manifestations of these diseases, and of selecting optimal treatment regimes for affected individuals.

TABLE A

SNP Markers Used for TDT and Association Analyses

| Gene Name | Marker | Chromosome | Position (bp)** |
|---|---|---|---|
| HPCAL1 | rs4668676 | 2p25.1 | 10,356,072 |
| HPCAL1 | rs6714483 | 2p25.1 | 10,362,983 |
| HPCAL1 | rs17882379 | 2p25.1 | 10,394,102 |
| HPCAL1 | rs6755271 | 2p25.1 | 10,427,491 |
| HPCAL1 | rs887973 | 2p25.1 | 10,431,133 |
| HPCAL1 | rs11893459 | 2p25.1 | 10,443,439 |
| HPCAL1 | rs2270299 | 2p25.1 | 10,453,937 |
| HPCAL1 | rs1808315 | 2p25.1 | 10,460,455 |
| HPCAL1 | rs11694643 | 2p25.1 | 10,470,378 |
| HPCAL1 | rs3732120 | 2p25.1 | 10,479,913 |
| HPCAL1 | rs12692407 | 2p25.1 | 10,491,404 |
| SV2C | rs889189 | 5q13.3 | 75,459,441 |
| SV2C | rs736005 | 5q13.3 | 75,483,802 |
| SV2C | rs6453211 | 5q13.3 | 75,549,151 |
| SV2C | rs4704298 | 5q13.3 | 75,549,821 |
| SV2C | rs1501926 | 5q13.3 | 75,569,146 |
| SV2C | rs11960621 | 5q13.3 | 75,603,754 |
| SV2C | rs2270927 | 5q13.3 | 75,627,466 |
| SV2C | rs31244 | 5q13.3 | 75,630,499 |

**The position shown is relative to NCBI Genome Build 36.3.

In one aspect, the invention includes methods for obtaining information regarding a human subject's risk for developing SZ or BD. The methods include obtaining a test haplotype associated with schizophrenia as or bipolar disorder as described herein, e.g., by determining the genotype (e.g., the identity of the allele) for one or more test markers as described herein. The methods can also include obtaining a sample comprising DNA, e.g., genomic DNA (gDNA), from the subject, and determining the identity, absence or presence of a test haplotype associated with SZ or BD as described herein. In some embodiments, the methods include obtaining a test haplotype for the subject comprising at least one test marker that is listed in Table A, or is in linkage disequilibrium with a marker listed in Table A, wherein the haplotype provides information regarding the subject's risk of developing SZ or BD. In some embodiments, the test marker is a marker listed in one or more of Table A, or a marker in linkage disequilibrium (i.e., D'>0.75 of a polymorphism described herein, e.g., markers in a region of chromosome 2p or 5q, e.g., in 2p between and including any two SNPs listed in Table A or Table B, e.g., SNPs rs4668676 and rs12692407 at the HPCAL1 locus; and/or in 5q, e.g., between and including any two SNPs listed in Table A or Table B, e.g., rs889189 and rs31244 at the SV2C locus. In some embodiments, the test haplotype includes at least one marker listed in Table A, e.g., two or more markers listed in Table A. In some embodiments, the test haplotype includes two or more markers from one gene, or from each gene if two or more genes are used. In some embodiments, the test haplotype includes at least two markers, each from a different gene listed in Table A.

In some embodiments, the methods further include obtaining a reference haplotype comprising a reference marker that corresponds to the test marker; and comparing the test haplotype to the reference haplotype, wherein the presence of a haplotype in both the test haplotype and a reference haplotype is indicative of whether there is an increased likelihood that a subject will develop SZ or BD.

Table B lists exemplary SNPs in linkage disequilibrium (LD) with the SNPs presented in Table A, which as one of skill in the art will appreciate can be used interchangeable with those SNPs in which they are in LD.

In some embodiments, the test haplotype includes at least one marker listed in Table A and provides information regarding a subject's risk of developing SZ or BD, under a narrower (DSM III/DSMIV) disease definition.

In some embodiments, the test haplotype provides information regarding a subject's risk of having a particular endophenotype, and/or one or more specific symptoms, e.g., hallucinations, paranoia, mania, depression, and/or obsessive-compulsive symptoms, as well as response or lack of response to drugs and comorbidity for substance and alcohol abuse.

The methods described herein can include obtaining a haplotype that includes two or more, e.g., two, three, four, five, or six markers. In some embodiments, additional markers can also be included e.g., ten, 25, 50, 100, or 1000 additional markers.

Additionally, the methods can include determining the presence or absence of other markers known to be associated with SZ or BD, e.g., outside of a region identified herein. A number of other such markers are known in the art, e.g., as described herein.

The subject can be a human (e.g., a patient having, or at risk of, SZ or BD). In one embodiment, the subject is a patient having SZ or BD (e.g., a patient suffering from early, intermediate, or aggressive SZ or BD). In some embodiments, the methods described herein are used to obtain information regarding a subject's risk of developing SZ, or BD, wherein the disorder is other than catatonic schizophrenia. In some embodiments, the subject is of African American (AA) or Caucasian (CA) descent, i.e., has one or more ancestors who are AA or CA.

In some embodiments, the methods include evaluating information regarding a subject's risk of developing SZ or BD further using haplotype information for the HPCAL1 gene or the SV2C gene, obtained using a method described herein, in combination with a haplotype or genotype for one or more genes described herein (e.g., listed in the section "Other Genetic Markers") with known associations to SZ and/or BD.

In one embodiment, a subject to be evaluated by a method described herein is a subject having one or more risk factors associated with SZ or BD, or the related schizophrenia-spectrum disorders, schizoaffective disorder (SD), or schizotypal personality disorder (SPD). For example, the subject may have a relative afflicted with SZ or BD, e.g., a first or second degree relative, e.g., one or more of a grandparent, parent, uncle or aunt, sibling, or child who has or had SZ, SD, SPD or BD; the subject may have a genetically based phenotypic trait associated with risk for SZ, SD, SPD or BD (e.g., eye tracking dysfunction); deficits in working (short-term) memory; and/or mixed-handedness (the use of different hands for different tasks), particularly in females.

In some embodiments, the subject is a child, fetus, or embryo, and one of the subject's relatives, e.g., a parent or sibling, of the child, fetus, or embryo has SZ, SD, SPD or BD. In this case, the presence in the child, fetus, or embryo of a haplotype described herein that is shared with the affected parent, but not with the non-affected parent, indicates that the child, fetus, or embryo has an increased risk of developing SZ, SD, SPD or BD. In some embodiments, the subject has no overt or clinical signs of SZ, SD, SPD or BD.

In some embodiments, obtaining a test haplotype includes obtaining a sample comprising DNA from the subject; and determining the identity, presence or absence of at least one test marker that is listed in Table A, or is in linkage disequilibrium (in the particular population) with a marker listed in Table A. The sample can be obtained, e.g., from the subject by a health care provider, or provided by the subject without the assistance of a health care provider.

In some embodiments, obtaining a test haplotype includes reviewing a subject's medical history, wherein the medical history includes information regarding the presence or absence of at least one test marker that is listed in Table A, or is in linkage disequilibrium with a marker listed in Table A.

In some embodiments, the methods described herein include obtaining a reference haplotype by obtaining a genotype for at least one reference marker that corresponds to a test marker, and comparing the test haplotype to the reference haplotype. A reference marker that "corresponds to" a test marker is the same marker. For example, if the test haplotype includes rs11893459, then the reference haplotype should also include rs11893459 for comparison purposes; or if the test haplotype includes rs889189, then the reference haplotype should also include rs889189 for comparison purposes. The sharing of a haplotype (e.g., of some or all of the markers) between the test haplotype and a reference haplotype is indicative of whether there is an increased likelihood that the subject will develop SZ or BD.

In some embodiments, the methods also include confirming a diagnosis of SZ or BD, using methods known in the art, e.g., psychometric instruments including rating scales for psychopathology and cognition and component subscales, e.g., BPRS, PANSS, quality of life scores (QLS).

In some embodiments, the methods include administering a treatment to a subject identified as being at increased risk for developing SZ or BD, e.g., a pharmacological or psychosocial treatment as described herein. In some embodiments, the subject has no overt or clinical signs of SZ, SD, SPD, or BD, and the treatment is administrated before any such signs appear.

In some embodiments, the test haplotype further provides information that differentiates patients that are more likely to respond to a treatment from those who are less likely to respond, or patients that are more likely to experience negative side effects from those less likely to experience negative side effects.

In some embodiments, the methods further include selecting or excluding a subject for enrollment in a clinical trial based on the test haplotype, or stratifying a subject population for analysis of a clinical trial based on the test haplotypes in the subjects. Thus information obtained using a method described herein can be used, e.g., to select a subject population for a clinical trial, to stratify a subject population in a clinical trial, and/or to stratify subjects that respond to a treatment from those who do not respond to a treatment, or subjects that have negative side effects from those who do not.

In another aspect, the invention provides methods for selecting a subject for inclusion in a clinical trial, e.g., a trial of a treatment for SZ, SD, SPD or BD. The methods include obtaining a obtaining a test haplotype for the subject, e.g., by determining the genotype for one or more test markers that is listed in Table A, or is in linkage disequilibrium with a marker listed in Table A; determining whether the haplotype is associated with altered drug response for patients with schizophrenia (SZ), schizotypal personality disorder (SPD), schizoaffective disorder (SD), or bipolar disorder (BD); and including the subject in the trial or excluding the subject from the trial if the haplotype indicates that the subject has altered drug response for patients with SZ, SD, SPD or BD.

In another aspect, the invention provides methods for selecting a subject for administration of a treatment for schizophrenia (SZ), schizotypal personality disorder (SPD), schizoaffective disorder (SD), or bipolar disorder (SD). The methods include obtaining a haplotype for the subject, wherein the haplotype comprises at least one marker that is listed in Table A, or is in linkage disequilibrium with a marker listed in Table A; determining whether the haplotype is associated with altered treatment response for patients with SZ, SD, SPD or BD; and administering the treatment to the subject if the haplotype indicates that the subject has an improved response to the treatment.

In another aspect, the invention provides methods for selecting a treatment for administration to a subject. The methods include obtaining a haplotype for the subject, e.g., obtaining a test haplotype for the subject by determining the genotype for one or more test markers that is listed in Table A, or is in linkage disequilibrium unit with a marker listed in Table A; determining whether the haplotype is associated altered treatment response for patients with schizophrenia (SZ), schizotypal personality disorder (SPD), schizoaffective disorder (SD), or bipolar disorder (BD); and administering the treatment for SZ, SD, SPD or BD to the subject if the haplotype indicates that the subject has an improved response to the treatment.

In another aspect, the invention provides methods for evaluating the effect of a haplotype on the outcome of a treatment for schizophrenia (SZ), schizotypal personality disorder (SPD), schizoaffective disorder (SD), or bipolar disorder (BD). The methods include obtaining information regarding outcome of the treatment, wherein the information comprises a parameter relating to the treatment of each subject in a population of subjects; obtaining haplotypes for each subject in the population, wherein the haplotype comprises at least one marker that is listed in Table A, or is in linkage disequilibrium with a marker listed in Table A; and correlating the information regarding outcome with the haplotypes; thereby evaluating the effect of the haplotype on the outcome of the treatment. In some embodiments, the one or more test markers are in the HPCAL1 gene between and including SNPs rs4668676 (SEQ ID NO:1) and rs12692407 (SEQ ID NO:11), or in the SV2C gene between and including SNPs rs889189 (SEQ ID NO: 12) and rs31244 (SEQ ID NO:19). In some embodiments, the one or more test markers are selected from the markers listed in Table A or Table B. The test haplotype indicates the subject's likely response to the treatment.

In a further aspect, the invention provides methods of predicting a subject's response to a treatment for schizophrenia (SZ), schizotypal personality disorder (SPD), schizoaffective disorder (SD), or bipolar disorder (BD). The methods include obtaining a test haplotype for the subject by determining the genotype for one or more test markers listed in Table A, or in linkage disequilibrium with a marker listed in Table A; and correlating the information regarding outcome with the haplotypes; thereby evaluating the effect of the haplotype on the outcome of the treatment. In some embodiments, the one or more test markers are in the HPCAL1 gene between and including SNPs rs4668676 (SEQ ID NO:1) and rs12692407 (SEQ ID NO:11), or in the SV2C gene between and including SNPs rs889189 (SEQ ID NO: 12) and rs31244 (SEQ ID NO:19). In some embodiments, the one or more test markers are selected from the markers listed in Table A or Table B. The test haplotype indicates the subject's likely response to the treatment.

In some embodiments, the method includes selecting a treatment for administration to a subject who has a selected haplotype, based on the effect of the haplotype on the outcome of the treatment.

In some embodiments, the information regarding outcome of the treatment is from a completed clinical trial, and the analysis is retrospective.

In another aspect, the invention features methods of predicting a subject's risk of developing SZ or BD. The methods include obtaining a reference haplotype. In some embodiments, the reference haplotype is from at least one of the following relatives of the subject: (i) a parent who has SZ, SD, SPD or BD; (ii) a sibling who has SZ, SD, SPD or BD, and an unaffected parent; or (iii) a second degree relative (e.g., aunt, uncle, or grandparent) who has SZ, SD, SPD or BD, and an unaffected parent; obtaining a test haplotype from the subject in the same region; and comparing the test haplotype to a reference haplotype. The presence of identity between the test haplotype and a reference haplotype from a relative having the disorder is an indication of an increased likelihood that the subject will develop SZ or BD. In some embodiments, the reference haplotype is from an unaffected individual, and sharing of a haplotype indicates that there is no increased likelihood that the subject will develop SZ or BD.

In a further aspect, the invention features methods for detecting the presence of a haplotype associated with susceptibility to SZ (broadly defined as including, in addition SD or SPD) or BD in a subject, by analyzing a sample of DNA from the subject.

Additionally, the invention features methods of predicting a test subject's risk of developing SZ or BD. The methods include obtaining a reference haplotype of a reference subject, wherein the reference subject has SZ or SD; determining a test haplotype of the test subject in the same region; and comparing the test haplotype to the reference haplotype, wherein the sharing of a haplotype in this region between the test subject and the reference subject is an indication of an increased likelihood that the test subject will develop SZ or BD. In some embodiments, the method further includes comparing the subject's haplotype to a reference subject who does not have SZ, SD, SPD or BD.

Further, the invention features methods for predicting a test subject's risk of developing SZ. The methods include obtaining a reference haplotype of a reference subject in a region described herein, wherein the reference subject has SZ; obtaining a test haplotype of the test subject in the same region; and comparing the test haplotype to the reference haplotype. The sharing of a haplotype in this region between the test subject and the reference subject is an indication of an increased likelihood that the test subject will develop SZ. In some embodiments, the method also includes comparing the test subject's haplotype to a reference subject who does not have SZ.

In another aspect, the invention features methods for predicting a subject's risk of developing a broadly defined disease condition encompassing either SZ, SD, SPD or BD. The methods include obtaining genomic DNA (gDNA) from the subject; and determining the absence or presence of a haplotype associated with SZ or BD as described herein. The presence of a haplotype associated with SZ or BD indicates that the subject has an increased risk of developing SZ, SD, SPD or BD.

Also provided herein are kits for use in detection of haplotypes associated with SZ, SD, SPD or BD, including at least one nucleic acid probe that hybridizes to a sequence that includes a polymorphism described herein, or can be used to amplify a sequence that includes a polymorphism described herein.

Also provided are arrays that include a substrate having a plurality of addressable areas, wherein one or more of the addressable areas includes one or more probes that can be used to detect a polymorphism described herein.

In another aspect, the invention provides methods for providing information regarding a subject's risk of developing schizophrenia (SZ), schizotypal personality disorder (SPD), schizoaffective disorder (SD), or bipolar disorder (BD). The methods include obtaining a sample from the subject at a first site; transferring the sample to a second site for analysis, wherein the analysis provides data regarding the identity, presence or absence of at least one test marker that is listed in Table A, or is in linkage disequilibrium with a marker listed in Table A; and transferring the data to one or more of a health care provider, the subject, or a healthcare payer. In some embodiments, the first site is a health care provider's place of business, or is not a health care provider's place of business, e.g., the subject's home.

In some embodiments, the data is transferred to a healthcare payer and used to decide whether to reimburse a health care provider.

Definitions

As defined herein, Schizophrenia includes Schizotypal Personality Disorder (SPD) and Schizoaffective Disorder (SD), as well as Schizophrenia under the narrower, DSM-IV definition (see below).

As used herein, a "haplotype" is one or a set of signature genetic changes (polymorphisms) that are normally grouped closely together on the DNA strand, are usually inherited as a group, and are associated together in the population due to linkage disequilibrium; the polymorphisms are also referred to herein as "markers." A "haplotype" as used herein is information regarding the presence or absence of one or more contiguous genetic markers on a given chromosome in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

Microsatellites (sometimes referred to as a variable number of tandem repeats or VNTRs) are short segments of DNA that have a repeated sequence, usually about 2 to 5 nucleotides long (e.g., CACACA), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

"Linkage disequilibrium" occurs when the observed frequencies of associations of alleles for different polymorphisms in a population do not agree with frequencies predicted by multiplying together the allele frequencies for the individual genetic markers, thus resulting in a specific haplotype in the population.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of particular markers or haplotypes described herein. The stratification can be performed, e.g., in the course of analysis, or can be used in creation of distinct groups or in other ways.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the invention will be apparent from the following detailed description and figures, and from the claims.

Tables

Table A lists SNP markers used for TDT and association analyses, as described herein. Location (BP) is relative to NCBI Genome Build 36.3.

Table B lists exemplary SNPs that are in linkage disequilibrium (D'>0.75) with the SNPs presented in Table A. Chrom., chromosome; Location (BP), base pair location relative to NCBI Genome Build 36.3.

Table C lists the human genomic DNA sequences for the SNPs listed in Table A. Square brackets designate the polymorphism.

DETAILED DESCRIPTION

The methods described herein are based, at least in part, on the discovery of haplotypes and markers that are associated with increased risk of having or developing schizophrenia (SZ) or bipolar disorder (BD). As described herein, analysis provided evidence of association of the disclosed SNPs and haplotypes with these disorders, with various clinical manifestations of the diseases, and with response to pharmacological interventions.

Methods of Diagnoses and Evaluation of Risk

Described herein are a variety of methods for the diagnosis of susceptibility to SZ or BD. "Susceptibility" does not necessarily mean that the subject will develop SZ or BD, but rather that the subject is, in a statistical sense, more likely to develop SZ or BD than an average member of the population, i.e., has an increased risk of developing SZ or BD. As used herein, susceptibility to SZ or BD exists if the subject has a haplotype associated with an increased risk of SZ or BD as described herein. Ascertaining whether the subject has such a haplotype is included in the concept of diagnosing susceptibility to SZ or BD as used herein. Such determination is useful, for example, for purposes of diagnosis, treatment selection, and genetic counseling. Thus, the methods described herein can include obtaining a haplotype associated with an increased risk of SZ or BD as described herein for the subject.

As used herein, "obtaining a haplotype" includes obtaining information regarding the identity, presence or absence of one or more genetic markers in a subject. Obtaining a haplotype can, but need not, include obtaining a sample comprising DNA from a subject, and/or assessing the identity, presence or absence of one or more genetic markers in the sample. The individual or organization who obtains the haplotype need not actually carry out the physical analysis of a sample from a subject; the haplotype can include information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

Obtaining a haplotype can also include or consist of reviewing a subject's medical history, where the medical history includes information regarding the identity, presence or absence of one or more genetic markers in the subject, e.g., results of a genetic test.

In some embodiments, to detect the presence of a haplotype described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for SZ or BD if the subject has an increased risk of developing SZ or BD. As another example, a drug or treatment may be indicated for individuals with a certain haplotype, and the insurance company would only reimburse the health care provider (or the insured individual) for prescription or purchase of the drug if the insured individual has that haplotype. The presence or absence of the haplotype in a patient may be ascertained by using any of the methods described herein.

Information gleaned from the methods described herein can also be used to select or stratify subjects for a clinical trial. For example, the presence of a selected haplotype described herein can be used to select a subject for a trial. The information can optionally be correlated with clinical information about the subject, e.g., diagnostic or endophenotypic information.

Haplotypes Associated with SZ, BD, or Pharmacological Response

The human genomic DNA sequences for the SNPs listed in Table A are listed in Table C (square brackets designate polymorphism):

Additionally, 18 SNPs in linkage disequilibrium with the SNPs in Table A were evaluated for impact on pharmacological response. The human genomic DNA sequences for those SNPs are listed in Table D (square brackets designate polymorphism).

As described herein, haplotypes associated with SZ or BD include markers in 2p25.1 (e.g., in HPCAL1), as exemplified by the transmission disequilibrium results shown in Tables 1, 2 and 3 and by the Case/Control results shown in Table 7; in 5q13.3 (e.g., in SV2C), as exemplified by the transmission disequilibrium results shown in Tables 4, 5 and 6 and by the Case/Control results in Tables 8 and 9.

As one example, haplotypes associated with a broad disorder definition of schizophrenia including SZ, SD, or SPD include one or more markers on chromosomes 2p, or 5q that are in linkage disequilibrium with markers listed in Tables 1, 2, 4, 5, 7, 8, or 9. In some embodiments, the haplotype includes one or more of the markers listed in Tables 1, 2, 4, 5, 7, 8, or 9. Haplotypes associated with a broader disorder definition of SZ or BD can include one or more markers that are in linkage disequilibrium with a marker listed in Tables 1, 2, 3, 4, 5, 6, 7, 8, or 9. In some embodiments, the markers are in a region of 2p25.1 that is between and including any two SNPs listed in Table A or Table B, e.g., SNPs rs4668676 and rs12692407 at the HPCAL1 locus. In some embodiments, the markers are in a region of 5q13.3 that is between and including any two SNPs listed in Table A or Table B, e.g., SNPs rs889189 and rs31244 at the SV2C locus.

As one example, haplotypes associated with a disease definition of BD include one or more markers on chromosomes 2p or 5q that are in linkage disequilibrium with a marker listed in Tables 3, 6, or 7. In some embodiments, the haplotype includes one or more of the markers listed in Tables 3, 6 or 7.

Haplotypes associated with a broader disorder definition of SZ or BD can include one or more markers that are in linkage disequilibrium with a marker listed in Tables 1, 2, 3, 4, 5, 6, 7, 8, or 9. In some embodiments, the markers are in a region of 2p25.1 that is between and including any two SNPs listed in Table A or Table B, e.g., SNPs rs4668676 and rs12692407 at the HPCAL1 locus. In some embodiments, the markers are in a region of 5q13.3 that is between and including any two SNPs listed in Table A or Table B, e.g., SNPs rs889189 and rs31244 at the SV2C locus.

In some embodiments, the gene is HPCAL1, and the rs887973(A)/rs11893459(C) haplotype is associated with disease. In some embodiments, the gene is SV2C, and the rs889189(A)/rs736005(C) haplotype is associated with increased risk of disease.

As one example, haplotypes associated with pharmacological response include one or more markers on chromosomes 2p or 5q that are in linkage disequilibrium with markers listed in Tables A as exemplified by the markers in Tables 10 and 11. Haplotypes associated with pharmacological response to antipsychotic medications can include one or more markers listed in Tables 10 and 11 and/or markers in linkage disequilibrium with these markers. In some embodiments, the haplotype includes one or more of the markers listed in Tables 10 and 11.

As another example, specific allelic combinations for a marker can be associated with altered pharmacological response. Genotypes associated with improved response to antipsychotic drugs for SZ are listed in table 10. Genotypes associated with increased side effects to antipsychotic drugs for SZ are listed in table 11.

In some embodiments, the markers are in a region of 2p25.1 that is between and including any two SNPs listed in Table A or Table B, e.g., SNPs rs4668676 and rs12692407 at the HPCAL1 locus. In some embodiments, the markers are in a region of 5q13.3 that is between and including any two SNPs listed in Table A or Table B, e.g., SNPs rs889189 and rs31244 at the SV2C locus.

In some embodiments, the methods include determining the presence of a haplotype that includes one or more polymorphisms at or near D22S526 and/or polymorphisms in the Sult4a1 gene and/or polymorphisms in linkage disequilibrium with one of these markers, e.g., as described in U.S. Pat. Pub. No. 2006-0177851, incorporated herein in its entirety.

In some embodiments, the methods include determining the presence of a haplotype that includes one or more polymorphisms in the PI4K2B gene and/or the polymorphisms in the KCNIP4 gene and/or polymorphisms in the CERK gene and/or polymorphisms in the SHANK3 gene and/or polymorphisms in linkage disequilibrium with one of these markers, e.g., as described PCT Pat. Application No. PCT/2007/07839960/640,707, incorporated herein in its entirety.

Hippocalcin-Like 1 Gene (HPCAL1)

The hippocalcin-like 1 gene (HPCAL1) is located on chromosome 2p (from 10,360,491 to 10,485,194 bp Genome Build: 36.3). It encodes neuron-specific calcium-binding protein, appears to be a paralog of the gene encoding the hippocalcin protein, and is highly conserved relative to rodent hippocalcin like-1 proteins. It is believed to be important for neuronal signaling in the central nervous system and is widely expressed in the brain (source: ncbi.nlm.nih.gov; NCBI Entrez Gene). The encoded protein is abnormally expressed in Alzheimer's Disease (see, e.g., Braunewell et al., Dement. Geriatr. Cogn Disord. 12:110-116 (2001)), but there is no prior evidence that the gene plays a role in SZ or BD disorder.

Synaptic Vesicle Glycoprotein 2C Gene (SV2C)

The synaptic vesicle glycoprotein 2C gene (SV2C) is located on chromosome 5q (from 75,415,061 to 75,657,172 bp Genome Build: 36.3; source: ncbi.nlm.nih.gov; NCBI Entrez Gene). It encodes the SV2C protein, which is expressed in the brain and interacts with synaptotagmin 1 to regulate neurotransmitter release in a variety of synapses (see, e.g., Lazzell et al., J. Biol. Chem. 279:52124-52131 (2004): Schivell et al., Mol. Cell Neurosci. 29:56-64 (2005); Xu et al., Nat. Cell Biol. 3:691-698 (2001); Janz et al., Neuroscience 94:1279-1290 (1999)).

Linkage Disequilibrium Analysis

Linkage disequilibrium (LD) is a measure of the degree of association between alleles in a population. One of skill in the art will appreciate that haplotypes involving markers within 1 Linkage Disequilibrium Unit (LDU; defined herein as D'>0.75, e.g., D'>0.8, >0.85, >0.9, >0.95, >0.99, or about 1) of the polymorphisms described herein can also be used in a similar manner to those described herein. LDUs share an inverse relationship with LD so that regions with high LD (such as haplotype blocks) have few LDUs and low recombination, whilst regions with many LDUs have low LD and high recombination. Methods of calculating LD and LDUs are known in the art (see, e.g., Morton et al., Proc Natl Acad Sci USA 98(9):5217-21 (2001); Tapper et al., Proc Natl Acad Sci USA 102(33):11835-11839 (2005); Maniatis et al., Proc Natl Acad Sci USA 99:2228-2233 (2002)).

Thus, in some embodiments, the methods include analysis of polymorphisms that are within 1 LDU of a polymorphism described herein. Methods are known in the art for identifying such polymorphisms; for example, the International HapMap Project provides a public database that can be used, see hapmap.org, as well as The International HapMap Consortium, Nature 426:789-796 (2003), and The International HapMap Consortium, Nature 437:1299-1320 (2005). Generally, it will be desirable to use a HapMap constructed using data from individuals who share ethnicity with the subject, e.g., a HapMap for African Americans would ideally be used to identify markers within 1 LDU of a marker described herein for use in genotyping a subject of African American descent.

Accordingly, methods described herein can include analysis of polymorphisms that are within a value defined by Lewontin's D' (linkage disequilibrium parameter, see Lewontin, Genetics 49:49-67 (1964)) of a polymorphism described herein. Results can be obtained, e.g., from on line public resources such as HapMap.org. The simple linkage disequilibrium parameter (D) reflects the degree to which alleles at two loci (for example two SNPs) occur together more often (positive values) or less often (negative values) than expected in a population as determined by the products of their respective allele frequencies. For any two loci, D can vary in value from −0.25 to +0.25. However, the magnitude of D (Dmax) varies as function of allele frequencies. To control for this, Lewontin introduced the D' parameter, which is D/Dmax and varies in value from −1 (alleles never observed together) to +1 (alleles always observed together). Typically, the absolute value of D' (i.e., |D'|) is reported in online databases, because it follows mathematically that positive association for one set of alleles at two loci corresponds to a negative association of equal magnitude for the reciprocal set. This disequilibrium parameter varies from 0 (no association of alleles at the two loci) to 1 (maximal possible association of alleles at the two loci).

Thus, in some embodiments, the methods include analysis of polymorphisms that are within D'>0.75, or D'=1, for pairwise comparisons, of a polymorphism described herein.

Identification of Additional Markers for Use in the Methods Described Herein

In general, genetic markers can be identified using any of a number of methods well known in the art. For example, numerous polymorphisms in the regions described herein are known to exist and are available in public databases, which can be searched using methods and algorithms known in the art. Alternately, polymorphisms can be identified by sequencing either genomic DNA or cDNA in the region in which it is desired to find a polymorphism. According to one approach, primers are designed to amplify such a region, and DNA from a subject is obtained and amplified. The DNA is sequenced, and the sequence (referred to as a "subject sequence" or "test sequence") is compared with a reference sequence, which can represent the "normal" or "wild type" sequence, or the "affected" sequence. In some embodiments, a reference sequence can be from, for example, the human draft genome sequence, publicly available in various databases, or a sequence deposited in a database such as GenBank. In some embodiments, the reference sequence is a composite of ethnically diverse individuals.

In general, if sequencing reveals a difference between the sequenced region and the reference sequence, a polymorphism has been identified. The fact that a difference in nucleotide sequence is identified at a particular site that determines that a polymorphism exists at that site. In most instances, particularly in the case of SNPs, only two polymorphic variants will exist at any location. However, in the case of SNPs, up to four variants may exist since there are four naturally occurring nucleotides in DNA. Other polymorphisms, such as insertions and deletions, may have more than four alleles.

Other Genetic Markers of Schizophrenia and Bipolar Disorder

The methods described herein can also include determining the presence or absence of other markers known or suspected to be associated with SZ, or with SD, SPD or BD, e.g., markers outside of a region identified herein, see, e.g., Harrison and Owen, Lancet, 361(9355):417-419 (2003), including, for example, markers on chromosome 22 and other chromosomes, e.g., in the region of 22q12.3 (e.g., near D22S283), 22q11.2, 22q11.2, 22q11-q13, 1q42.1, 1q42.1, 1q21-q22, 2p, 2q, 3p25, 4p, 4q, 5q11.2-q13.3, 6p22.3, 6p23, 6q13-q26, 7q, 8p12-21, 8q, 9p, 10p15-p13 (e.g., near D10S189), 10q22.3, 11q14-q21, 12q24, 13q34, 13q32, 14q32.3, 15q15, 16p, 17q, 18p, 18q, 19p. 20p, 21q, Xq, and/or the X/Y pseudoautosomal region. In some embodiments, the methods include determining the presence or absence of one or more other markers that are or may be associated with SZ, or with SZ, SD or SPD, e.g., in one or more genes, e.g., ACE (Illi et al., Eur Neuropsychopharmacol 13:147-151 (2003)); ADRA1A (Clark et al., Biol Psychiatry. 58(6):435-9 (2005)); ADH1B (Xu et al., Mol Psychiatry. 9(5):510-21 (2004); Vawter et al., Hum Genet. 119(5):558-70 (2006)); AHI1 (Eur J Hum Genet. 14(10): 1111-9 (2006)); AKT1 (Emamian et al., Nature Genet. 36:131-137 (2004)); ALDH3B1 (Sun et al. Sci. China C. Life. Sci. 48(3):263-9 (2005)); ALK (Kunagi et al., J Neural Transm. 113(10):1569-73 (2006)); APC (Cui et al., Mol Psychiatry (7):669-77 (2005)); APOE (Liu et al., Schizophr Res 62: 225-230 (2003)); ARSA (Marcao et al., Mol Genet Metab. 79(4):305-7 (2003); ARVCF (Chen et al., Schizophr Res. 72(2-3):275-7 (2005)); ATXN1 (Pujana et al Hum Genet 99:772-775 (1997); Joo et al., Psychiatr Genet 9:7-11 (1999); Fallin et al., Am J Hum Genet 77:918-936 (2005)); BDNF (Neves-Pereira et al., Molec. Psychiat. 10:208-212 (2005)); BRD1 (Severinsen et al., Mol Psychiatry. 11(12):1126-38 (2006)); BZRP (Kurumaji et al., J Neural Transm. 107(4): 491-500 (2000)); DAO (Owen et al., Trends Genet. 21(9): 518-25 (2005)); DAOA (Owen et al., 2005, supra); CAPON (Brzustowicz et al., Am J Hum Genet. 74(5):1057-63 (2004)); CCKAR (Zhang et al., Mol Psychiatry 5:239-240 (2000); Sanjuan et al., Eur Psychiatry 19:349-353 (2004)); CHGB (Kitao et al., Psychiatr Genet 10:139-143 (2000); Zhang et al., Neurosci Lett 323:229-233 (2002)); CHI3L1 (Zhao et al., Am J Hum Genet. 80(1):12-8 (2007)); CHRNA2 (Blaveri et al., Europ. J. Hum. Genet. 9: 469-472 (2001)); CHRNA7 (Leonard et al. Arch Gen Psychiatry. 2002 59:1085-1096 (2002); De Luca et al. Neuropsychobiology. 50:124-127 (2004)); CLDN5 (Sun et al., Eur Psychiatry 19:354-357 (2004); Wei and Hemmings, Prostaglandins Leukot Essent Fatty Acids 73(6)4:41-445 (2005)); COMT (Shifman et al., Am. J. Hum. Genet. 71:1296-1302 (2002)); CNR1 (Ujike et al., Mol Psychiatry 7:515-518 (2002)); CPLX2 (Lee et al., Behav Brain Funct. 1:15 (2005)); DGCR8 (Jacquet et al., Hum Mol Genet. 11(19):2243-9 (2002)); DISC1 (Owen et al., 2005, supra; see, e.g., the D1S2709 marker (Ekelend et al., Hum. Molec. Genet. 10:1611-1617 (2001), DDR1 (Roig et al., Mol Psychiatry. 12(9); 833-41 (2007); DRD4 (Lung et al., Schizophr Res 57:239-245 (2002)); DDR3 (Williams et al., Mol Psychiatry 3:141-149 (1998)); DRD5 (Williams et al., Psychiatr Genet. 7:83-85 (1997); Muir et al., Am J Med Genet 105:152-158 (2001)); HEP3 haplotype, Hennah et al., Hum. Molec. Genet. 12: 3151-3159 (2003), and Leu607Pro, Hodgkinson et al., Am. J. Hum. Genet. 75:862-872 (2004), Erratum: Am. J. Hum. Genet. 76:196 (2005)); DISC2 (Millar et al., Ann Med. 36(5):367-78 (2004)); DPYSL2 (Hong et al., Am J Med Genet B Neuropsychiatr Genet. 136(1):8-11 (2005)); DRD1 (Coon et al., Am. J. Hum. Genet. 52: 327-334 (1993)); DRD2 (Glatt et al., Am. J. Psychiat. 160:469-476 (2003)); DRD3 (Rybakowski et al., Molec. Psychiat. 6:718-724 (2001)); DTNBP1 (Owen et al., 2005, supra); EGR3 (Yamada et al., Proc Natl Acad Sci 104(8):2815-20 (2007)); EPSIN4 (Am J Hum Genet. 76(5):902-7 (2005)); ErbB; EGF (Futamura et al., Am. J. Hum. Genet. 52: 327-334 (2002)); ENTH (Pimm et al., Am J Hum Genet 76:902-907 (2005); Tang et al, Mol Psychiatry 11:395-399 (2006)); ERBB4 (Norton et al., Am J Med Genet B Neuropsychiatr Genet 14; 11; 96-101 (2005); Silberberg et al., Am J Med Genet B Neuropsychiatr Genet 141B; 2; 142-148 (2006)); FEZ1 (Yamada et al., Biol Psychiatry 56:683-690(2004)); FOXP2 (Sanjuan et al., Psychiatr Genet. 16(2):67-72 (2006)); FXYD6 (Choudhury et al., Am J Hum Genet. 80(4):664-72 (2007)); FZD3 (Katsu et al., Neurosci Lett 353:53-56 (2003); Yang et al., Biol Psychiatry 54:1298-1301 (2003); Zhang et al., Am J Med Genet 129B:16-19 (2004)); GABRA1, GABRA2, GABRA6, GABRP (Petryshen et al., Mol Psychiatry. 10(12):1057 (2005)); GABBR1 (Zai et al. Eur Neuropsychopharmacol. 15:347-52 (2005); Le-Niculescu et al. Am J Med Genet B Neuropsychiatr Genet. 144:129-58 (2007)); GAD1 (Addington et al., Mol Psychiatry 10:581-588 (2005)); GFRA1 (Semba et al., Brain Res Mol Brain Res. 124(1):88-95 (2004)); GCLM (Tosic et al., Am J Hum Genet. 79(3):586-92 (2006)); GNB3 (Kunugi et al., J. Neural Transm. 109(2):213-8 (2002)); GPR78 (Underwood et al., Mol Psychiatry. 11(4):384-94 (2006)); GRIA1 (Magri et al., Am J Med Genet B Neuropsychiatr Genet 141(3):287-93 (2006)); GNPAT (Lin et al., Biol Psychiatry. 60(6):554-62 (2006)); GRID1 (Fallin et al., Am J Hum Genet 77:918-936 (2005)); GRIK1 (Shibata et al., Psychiatr Genet. 11(3):139-44 (2001)); GRIK2 (Shibata et al., Psychiatry Res. 113(1-2): 59-67 (2002)); GRIK3 (Shibata et al., Psychiatry Res. 30: 141(1): 39-51 (2006)); GRIK4 (Pikard et al., Mol Psychiatry 11(9):847-57 (2006)); GRIN1 (Qin et al., Eur J Hum Genet. 13(7):807-14 (2005)); GRIN2A, GRIN2B (Abdolmaleky et al., Am J Pharmacogenomics. 5(3):149-60 (2005)); GRIN2D (Makino et al., Psychiatr Genet. 15(3):215-21 (2005)); GRM3 (Egan et al., Proc Natl Acad Sci USA. 101(34):12604-9 (2004)); GRM4 (Ohtsuki et al., Psychiatr Genet. 11(2):79-83 (2001)); GRM5 (Devon et al., Mol Psychiatry. 6(3):311-4 (2001)); GSTM1 (Harada et al., Biochem Biophys Res Commun 281:267-271 (2001); Pae et al., Psychiatr Genet 14:147-150 (2004)); G30/G72 (Schulze et al., Am J Psychiatry. 162(11):2101-8 (2005)); HTR2A (Baritaki et al., Eur J Hum Genet. 12(7):535-41 (2004)); HLA-DRB1 (Schwab et al., Am J Med Genet. 114(3):315-20 (2002)); HLA-BRB3 (Yu et al., Zhonghua Liu Xing Bing Xue Za Zhi. 24(9):815-8 (2003)); HTR5A (Abdolmaleky et al., Schizophr Res 67:53-62 (2004)); HTR6 (Tsai et al., Neurosci Lett. 271 (2):135-7 (1999)); IL1B (Katila et al., Mol Psychiatry 4:179-181 (1999); Meisenzahal et al., Am J Psychiatry 158:1316-1319 (2001); Zanardini et al., J Psychiatr Res 37:457-462 (2003)); IL1RN (Zanardini et al., J Psychiatr Res 37:457-462 (2003); Kim et al., Psychiatr Genet 14:165-167 (2004); Papiol et al., Neuroimage 27:1002-1006 (2005)); IL10 (Chiavetto et al., Biol Psychiatry 51:480-484 (2002); Jun et al., Psychiatry Clin Neurosci 56:177-180 (2002)); IL2RB (Schwab et al., Am J Med Genet. 60(5):436-43 (1995)); KCNN3 (Ujike et al., Psychiatry Res. 101(3):203-7 (2001)); KIF13A (Jamain et al., Genomics. 74(1):36-44 (2001)); KIF2A (Li et al., Neurosci Letters 407(2) 151-5 (2006)); KPNA3 (Wei and Hemmings, Neurosci Res. 52(4):342-6 (2005)); LGI1 (Fallin et al. A J Hum Genet. 77:918-36 (2005)); MAG (Wan et al., Neurosci Lett. 388(3):126-31 (2005)); MAOA (Jonsson et al., Schizophr Res 61:31-37 (2003); Wei and Hemmings. Psychiatr Genet 9, 177-181 (1999)); MED12 (Sandhu et al., Am J Med Genet B Neuropsychiatr Genet. 123B: 33-38 (2003); Spinks et al., Am J Med Genet B Neuropsychiatr Genet. 127B:20-27 (2004)); MLC1 (Verma et al., Biol Psychiatry. 58(1):16-22 (2005)); MTHFR (Lewis et al., Am. J. Med. Genet. (Neuropsychiat. Genet.) 135B:2-4 (2005)); MTR (Kempisty et al., Psychiatr Genet. 17(3):177-81 (2007)); MTHFD1 (Kempisty et al., Psychiatr Genet. 17(3):177-81 (2007)); NCAM1 (Sullivan et al., Biol Psychiatry. 61(7):902-10 (2007)); NDE1 (Hennah et al., Hum Mol Genet. 16(5):453-62 (2006)); NDUFV2 (Waskizuka et al., Am J Med Genet B Neuropsychiatr Genet. 141(3):301-4

(2006)); NOS1 (Liou et al., Schizophr Res. 65(1):57-9 (2003)); NOTCH4 (Wei and Hemmings, (Letter) Nature Genet. 25:376-377 (2000)); NPAS3 (Kamnasaran et al., J Med Genet 40:325-332 (2003)); NRG1 (Owen et al., 2005, supra); NRG3 (Fallin et al. A J Hum Genet. 77:918-36 (2005)); NTNG1 (Fukawasa et al., J Med Dent Sci 51:121-128 (2004); Aoki-Suzuki et al., Biol Psychiatry 57:382-393 (2005)); NTNG2 (Aoki-Suzuki et al., Biol Psychiatry 57:382-393 (2005)); NTF3 (Jonsson et al., Acta Psychiatr Scand 95:414-419 (1997)); OLIG2 (Georgieva et al., Proc Natl Acad Sci 103(33):12469-74 (2006)); PCQAP (Sandhu et al., Psychiatr Genet. 14(3):169-72 (2004)); PDE4B (Millar et al., Science 310:1187-1191 (2005)); PDLIM5 (Horiuchi et al., Biol Psychiatry 59(5):434-9 (2005)); PICK1 (Hong et al., Neuroreport 15:1965-1967 (2004); Fujii et al., Molecular Psychiatry 11:150-157 (2005)); PIK3C3 (Stopkova et al., Biol Psychiatry 55:981-988 (2004); Duan et al., Neurosci Lett., 379:32-36 (2005)); PIK4CA (Saito et al., Am J Med Genet B Neuropsychiatr Genet. 116(1):77-83 (2003)); PIP5K2A (Stopkova et al., Psychiatr Genet. 15(3): 223-7 (2005)); PLA2G4A, PLA2G4C (Yu et al., Prostaglandins Leukot Essent Fatty Acids. 73(5):351-4 (2005)); PLA2G4B (Tao et al., Am J Med Genet B Neuropsychiatr Genet 137:56-58 (2005)); PLXNA2 (Mah et al., Molecular Psychiatry 11:471-478 (2006)); PTGS2 (Wei and Hemmings. Prostaglandins Leukot Essent Fatty Acids 70:413-415 (2004)); PPP3CC (Gerber et al., Proc Natl Acad Sci USA. 100(15): 8993-8 (2003)); PNOC (Blaveri et al., 2001); PRODH (Chakravarti, Proc. Nat. Acad. Sci. 99:4755-4756 (2002)); QKI (Aberg et al., Am J Med Genet B Neuropsychiatr Genet. 2005 Dec. 9; [Epub ahead of print]); RGS4 (Chowdari et al., Hum. Molec. Genet. 11:1373-1380 (2002), Erratum: Hum. Molec. Genet. 12:1781 (2003)); RELN (Costa et al., Mol Interv. 2(1):47-57 (2002)); RTN4 (Novak et al., Brain Res Mol Brain Res 107:183-189 (2002); Tan et al., Brain Res Mol Brain Res 139:212-216 (2005)); SCAT (Culkjovic et al., Am J Med Genet. 96(6):884-7 (2000)); SLC15A1 (Maheshwari et al., BMC Genomics. 3(1):30 (2002)); SLC18A1 (Bly, Schizophr Res. 78(2-3):337-8 (2005)); SLC18A2 (Gutierrez et al. Am J Med Genet B Neuropsychiatr Genet. 144(4):502-7 (2007)); SLC6A4 (Fan and Sklar, Mol Psychiatry. 10(10): 928-38, 891 (2005)); SNAP29 (Saito et al., Mol Psychiatry 6(2):193-201 (2001); Erratum in: Mol Psychiatry 6(5):605 (2001); SULT4A1 (Brennan and Chondra. Am J Med Genet B Neuropsychiatr Genet. 139(1):69-72 (2005)); SYNGR1 (Verma et al., Biol Psychiatry. 55(2):196-9 (2004)); SYN2 (Chen et al., Bio. Psychiat. 56:177-181 (2004)); SYN3 (Porton et al. Biol Psychiatry. 55(2):118-25 (2004)); TAAR4 (Duan et al., Am J Hum Genet 75:624-638 (2004)); TBP/SCA17 (Chen et al., Schizophr Res. 78(2-3):131-6 (2005)); TH (Kurumaji et al., Neural Transm 108:489-495 (2001); Meloni et al., C R Acad Sci III 318:803-809 (1995)); TNFA (Morar et al., Am J Med Genet B Neuropsychiatr Genet. 144(3):318-24 (2007)); TPH1 (Nolan et al., Psychiatr Genet 10:109-115 (2000); Hong et al., Schizophr Res 49:59-63 (2001); Sekizawa et al., Am J Med Genet B Neuropsychiatr Genet 128:24-26 (2004)); TPP2 (Fallin et al. A J Hum Genet. 77:918-36 (2005)); TPS3 (Park et al., Schizophr Res 67:71-74 (2004); Ni et al., Neurosci Lett 388:173-178 (2005)); TRAR4 (Am J Hum Genet. 75(4):624-38 (2004)); TRAX (Thomson et al., Mol Psychiatry. 10(7):657-68, 616 (2005)); UFD1L (De Luca et al., Am J Med Genet. 105(6):529-33 (2001)); UCP2 (Yasuno et al., Am J Med Genet B Neuropsychiatr Genet. 144(2):250-3 (2007)); UCP4 (Yasuno et al., Am J Med Genet B Neuropsychiatr Genet. 144(2):250-3 (2007)); UHMK1 (Puri et al., Biol Psychiatry 61(7):873-9 (2007)); XBP1 (Chen et al., Biochem Biophys Res Commun 319:866-870 (2004); Kakiuchi et al., Psychiatry Clin Neurosci 58:438-440 (2004)); YWHAH (Toyooka et al., Am J Med Genet. 88(2):164-7 (1999)); ZDHHC8 (Mukai et al., Nature Genet. 36:725-731 (2004)); or ZNF74 (Takase et al., Schizophr Res. 52(3):161-5 (2001)). See also, e.g., OMIM entry no. 181500 (SCZD).

In some embodiments, the methods include determining the presence of a haplotype that includes one or more polymorphisms near D22S526 and/or the polymorphisms in the Sult4a1 gene and/or polymorphisms within 1 LDU of these markers, e.g., as described in U.S. Pat. Pub. No. 2006-0177851, incorporated herein in its entirety.

In some embodiments, the methods include determining the presence of a haplotype that includes one or more polymorphisms in the PI4K2B gene and/or the polymorphisms in the KCNIP4 gene and/or polymorphisms in the CERK gene and/or polymorphisms in the SHANK3 gene and/or polymorphisms within 1 LDU of these markers, e.g., as described PCT Pat. Application No. PCT/2007/07839960/640,707, incorporated herein in its entirety.

Methods of Determining the Presence or Absence of a Haplotype Associated with SZ or BD The methods described herein include determining the presence or absence of haplotypes associated with SZ, SD, SPD or BD. In some embodiments, an association with SZ or BD is determined by the presence of a shared haplotype between the subject and an affected reference individual, e.g., a first or second-degree relation of the subject, and the absence of the haplotype in an unaffected reference individual. Thus the methods can include obtaining and analyzing a sample from a suitable reference individual.

Samples that are suitable for use in the methods described herein contain genetic material, e.g., genomic DNA (gDNA). Non-limiting examples of sources of samples include urine, blood, and tissue. The sample itself will typically consist of nucleated cells (e.g., blood or buccal cells), tissue, etc., removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

The absence or presence of a haplotype associated with SZ or BD as described herein can be determined using methods known in the art, e.g., gel electrophoresis, capillary electrophoresis, size exclusion chromatography, sequencing, and/or arrays to detect the presence or absence of the marker(s) of the haplotype. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, Northern analysis, or in situ hybridizations, can also be used (see *Current Protocols in Molecular Biology*, Ausubel, F. et al., eds., John Wiley & Sons 2003). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

Other methods include direct manual sequencing (Church and Gilbert, Proc. Natl. Acad. Sci. USA 81:1991-1995 (1988); Sanger et al., Proc. Natl. Acad. Sci. 74:5463-5467 (1977); Beavis et al. U.S. Pat. No. 5,288,644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., Proc. Natl. Acad. Sci. USA 86:232-236 (1989)), mobility shift analysis (Orita et al., Proc. Natl. Acad. Sci. USA 86:2766-2770 (1989)), restriction enzyme analysis (Flavell et al., Cell 15:25 (1978); Geever et al., Proc. Natl. Acad. Sci. USA 78:5081 (1981)); quantitative real-time PCR (Raca et al., Genet Test 8(4):387-94 (2004)); heteroduplex analysis; chemical mismatch cleavage (CMC) (Cotton et al., Proc. Natl. Acad. Sci. USA 85:4397-4401 (1985)); RNase protection assays (Myers et al., Science 230:1242 (1985)); use of polypeptides that recognize nucleotide mismatches, e.g., *E. coli* mutS protein; allele-specific PCR, for example. See, e.g., U.S. Patent Publication No. 2004/0014095, to Gerber et al., which is incorporated herein by reference in its entirety. In some embodiments, the methods described herein include determining the sequence of the entire region of the HPCAL1 locus described herein as being of interest, e.g., between and including any two SNPs listed in Table A or Table B, e.g., SNPs rs4668676 and rs12692407. In some embodiments, the methods described herein include determining the sequence of the entire region of the SV2C locus described herein as being of interest, e.g., between and including any two SNPs listed in Table A or Table B, e.g., SNPs rs889189 and rs31244. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., *PCR Primer: A Laboratory Manual*, Dieffenbach and Dveksler, (Eds.); McPherson et al., *PCR Basics: From Background to Bench* (Springer Verlag, 2000); Mattila et al., Nucleic Acids Res., 19:4967 (1991); Eckert et al., *PCR Methods and Applications*, 1:17 (1991); PCR (eds. McPherson et al., IRL Press, Oxford); and U.S. Pat. No. 4,683,202. Other amplification methods that may be employed include the ligase chain reaction (LCR) (Wu and Wallace, Genomics, 4:560 (1989), Landegren et al., Science, 241:1077 (1988), transcription amplification (Kwoh et al., Proc. Natl. Acad. Sci. USA, 86:1173 (1989)), self-sustained sequence replication (Guatelli et al., Proc. Nat. Acad. Sci. USA, 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a haplotype as described herein. The haplotype can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to or indicative of the presence of SZ.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of the presence or absence of susceptibility to SZ.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., Nature (London) 324:163-166 (1986)). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for particular a polymorphism can be prepared using standard methods (see Ausubel et al., *Current Protocols in Molecular Biology*, supra).

Generally, to determine which of multiple polymorphic variants is present in a subject, a sample comprising DNA is obtained from the individual. PCR can be used to amplify a portion encompassing the polymorphic site. DNA containing the amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to SZ) to DNA from the subject is indicative of susceptibility to SZ.

In some embodiments, fluorescence polarization template-directed dye-terminator incorporation (FP-TDI) is used to determine which of multiple polymorphic variants of a polymorphism is present in a subject (Chen et al., (1999) Genome Research, 9(5):492-498)). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., (2000) Genome Research, 10(8): 1249-1258). Additional methods include, for example, PCR amplification in combination with denaturing high performance liquid chromatography (dHPLC) (Underhill, P. A., et al., Genome Research, Vol. 7, No. 10, pp. 996-1005, 1997).

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multiwell plate or other vessel may also be performed so as to detect the presence of multiple polymorphic variants (e.g., polymorphic variants at a plurality of polymorphic sites) in parallel or substantially simultaneously according to certain embodiments of the invention.

Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence. The probe sequence must also be sufficiently long so that the probe exhibits selectivity for the target sequence over non-target sequences. For example, the probe will be at least 20, e.g., 25, 30, 35, 50, 100, 200, 300, 400, 500, 600, 700, 800, 900 or more, nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., polymorphisms as described herein. In some embodiments, the probe can hybridize to a target sequence within a region delimited by SNP rs4668676 and SNP rs12692407. In some embodiments, the probe can hybridize to a target sequence within a region delimited by SNP rs889189 and SNP rs31244. In some embodiments, the probe can bind to another marker sequence associated with SZ or BD as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic. Histochem., 1998, 73(1):6-22, Wheeless et al., Cytometry 1994, 17:319-326, and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and -6)-carboxy-X-rhodamine, lissamine rhodamine B, 5-(and -6)-carboxyfluorescein, fluorescein-5-isothiocyanate (FITC), 7-diethylaminocoumarin-3-carboxylic acid, tetramethyl-rhodamine-5-(and -6)-isothiocyanate, 5-(and -6)-carboxytetramethylrhodamine, 7-hydroxycoumarin-3-carboxylic acid, 6-[fluorescein 5-(and -6)-carboxamido]hexanoic acid, N-(4, 4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Arrays and Uses Thereof

In another aspect, the invention features arrays that include a substrate having a plurality of addressable areas, and methods of using them. At least one area of the plurality includes a nucleic acid probe that binds specifically to a sequence comprising a polymorphism listed in Table A, and can be used to detect the absence or presence of said polymorphism, e.g., one or more SNPs, microsatellites, minisatellites, or indels, as described herein, to determine a haplotype. For example, the array can include one or more nucleic acid probes that can be used to detect a polymorphism listed in Table A. In some embodiments, the array further includes at least one area that includes a nucleic acid probe that can be used to specifically detect another marker associated with SZ or BD as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 2p, 5q and/or 10q, e.g., a region between and including any two SNPs listed in Table A or Table B, e.g., SNPs rs4668676 and rs12692407, e.g., a region between and including any two SNPs listed in Table A or Table B, e.g., SNPs rs889189 and rs31244, and optionally a different portion of genomic DNA, e.g., a portion that includes a different portion of human chromosomes 2, 5 and/or 10, or another chromosome, e.g., including another region associated with SZ, SD, SPD or BD, and detecting binding of a nucleic acid from the sample to the array. Optionally, the method includes amplifying nucleic acid from the sample, e.g., genomic DNA that includes a portion of a human chromosome described herein, and, optionally, a region that includes another region associated with SZ, SD, SPD or BD, prior to or during contact with the array.

In some aspects, the methods described herein can include using an array that can ascertain differential expression patterns or copy numbers of one or more genes in samples from normal and affected individuals (see, e.g., Redon et al., Nature. 444(7118):444-54 (2006)). For example, arrays of probes to a marker described herein can be used to measure polymorphisms between DNA from a subject having SZ or BD, and control DNA, e.g., DNA obtained from an individual that does not have SZ or BD and has no risk factors for SZ or BD. Since the clones on the array contain sequence tags, their positions on the array are accurately known relative to the genomic sequence. Different hybridization patterns between DNA from an individual afflicted with SZ or BD and DNA from a normal individual at areas in the array corresponding to markers in human chromosome 2p and/or 5q as described herein, and, optionally, one or more other regions associated with SZ or BD, are indicative of a risk of SZ or BD. Methods for array production, hybridization, and analysis are described, e.g., in Snijders et al., (2001) *Nat. Genetics* 29:263-264; Klein et al., (1999) Proc. Natl. Acad. Sci. U.S.A. 96:4494-4499; Albertson et al., (2003) Breast Cancer Research and Treatment 78:289-298; and Snijders et al. "BAC microarray based comparative genomic hybridization." In: Zhao et al. (eds), *Bacterial Artificial Chromosomes: Methods and Protocols*, Methods in Molecular Biology, Humana Press, 2002. Real time quantitative PCR can also be used to determine copy number.

In another aspect, the invention features methods of determining the absence or presence of a haplotype associated with SZ or BD as described herein, using an array described above. The methods include providing a two dimensional array having a plurality of addresses, each address of the plurality being positionally distinguishable from each other address of the plurality having a unique nucleic acid capture probe, contacting the array with a first sample from a test subject who is suspected of having or being at risk for SZ or BD, and comparing the binding of the first sample with one or more references, e.g., binding of a sample from a subject who is known to have SZ or BD, and/or binding of a sample from a subject who is unaffected, e.g., a control sample from a subject who does not SZ or BD and is not at familial risk of developing SZ or BD. In some embodiments, the methods include contacting the array with a second sample from a subject who has SZ or BD; and comparing the binding of the first sample with the binding of the second sample. In some embodiments, the methods include contacting the array with a third sample from a subject (or a cell line derived from a subject) that does not have SZ or BD and has no familial risk for SZ or BD; and comparing the binding of the first sample with the binding of the third sample. In some embodiments, the second and third samples are from first or second-degree relatives of the test subject. Binding, e.g., in the case of a nucleic acid hybridization, with a capture probe at an address of the plurality, can be detected by any method known in the art, e.g., by detection of a signal generated from a label attached to the nucleic acid.

Schizophrenia and Bipolar Disorder

The methods described herein can be used to determine an individual's risk of developing schizophrenia (SZ) and/or bipolar disorder (BD).

Schizophrenia (SZ)

SZ is considered a clinical syndrome, and is probably a constellation of several pathologies. Substantial heterogeneity is seen between cases, which is thought to reflect multiple overlapping etiologic factors, including both genetic and environmental contributions. A diagnosis of SZ is typically indicated by chronic psychotic symptoms, e.g., hallucinations and delusions. Disorganization of thought and behavior are common and are considered distinguishing factors in the diagnosis of SZ. Patients typically have some subtle impairments in cognition. Reduced emotional experience and expression, low drive, and impaired speech are observed in a subgroup of patients. Cognitive, emotional and social impairments often appear early in life, while the psychotic symptoms typically manifest in late adolescence or early adulthood in men, a little later in women.

A diagnosis of SZ can be made according to the criteria reported in the *Diagnostic and Statistical Manual of Mental Disorders, Fourth Edition, Text Revision*, American Psychiatric Association, 2000, (referred to herein as DSM-IV) as follows:

Diagnostic Criteria for SZ

All six criteria must be met for a diagnosis of SZ.

A. Characteristic symptoms: Two (or more) of the following, each present for a significant portion of time during a one month period (or less if successfully treated):

(1) delusions
(2) hallucinations
(3) disorganized speech (e.g., frequent derailment or incoherence)
(4) grossly disorganized or catatonic behavior
(5) negative symptoms, e.g., affective flattening, alogia, or avolition Only one criterion A symptom is required if delusions are bizarre or hallucinations consist of a voice keeping up a running commentary on the person's behavior or thoughts, or two or more voices conversing with each other.

B. Social/occupational dysfunction: For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration: Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

D. Schizoaffective and Mood Disorder Exclusion: Schizoaffective Disorder and Mood Disorder With Psychotic Features have been ruled out because either (1) no major depressive, manic, or mixed episodes have occurred concurrently with the active-phase symptoms; or (2) if mood episodes have occurred during active-phase symptoms, their total duration has been brief relative to the duration of the active and residual periods.

E. Substance/General Medical Condition Exclusion: The disturbance is not due to the direct physiological effects of a substance (e.g., a drug of abuse, a medication) or a general medical condition.

F. Relationship to a Pervasive Developmental Disorder: If the patient has a history of Autistic Disorder or another Pervasive Developmental Disorder, the additional diagnosis of SZ is made only if prominent delusions or hallucinations are also present for at least a month (or less if successfully treated).

Schizoaffective Disorder (SD)

SD is characterized by the presence of affective (depressive or manic) symptoms and schizophrenic symptoms within the same, uninterrupted episode of illness.

Diagnostic Criteria for Schizoaffective Disorder

The DSM-IV Criteria for a diagnosis of schizoaffective disorder is as follows:

An uninterrupted period of illness during which, at some time, there is either (1) a Major Depressive Episode (which must include depressed mood), (2) a Manic Episode, or (3) a Mixed Episode, concurrent with symptoms that meet (4) Criterion A for SZ, above.

A. Criteria for Major Depressive Episode

At least five of the following symptoms must be present during the same 2-week period and represent a change from previous functioning; at least one of the symptoms is either (1) depressed mood or (2) loss of interest or pleasure.

(1) depressed mood most of the day, nearly every day, as indicated by either subjective report (e.g., feels sad or empty) or observation made by others (e.g., appears tearful). In children and adolescents, this can be an irritable mood.

(2) markedly diminished interest or pleasure in all, or almost all, activities most of the day, nearly every day (as indicated by either subjective account or observation made by others)

(3) significant weight loss when not dieting or weight gain (e.g., a change of more than 5% of body weight in a month), or decrease or increase in appetite nearly every day. (In children, failure to make expected weight gains is considered).

(4) insomnia or hypersomnia nearly every day (5) psychomotor agitation or retardation nearly every day (observable by others, not merely subjective feelings of restlessness or being slowed down)

(6) fatigue or loss of energy nearly every day (7) feelings of worthlessness or excessive or inappropriate guilt (which may be delusional) nearly every day (not merely self-reproach or guilt about being sick)

(8) diminished ability to think or concentrate, or indecisiveness, nearly every day (either by subjective account or as observed by others)

(9) recurrent thoughts of death (not just fear of dying), recurrent suicidal ideation without a specific plan, or a suicide attempt or a specific plan for committing suicide In addition, the symptoms do not meet criteria for a Mixed Episode. The symptoms cause clinically significant distress or impairment in social, occupational, or other important areas of functioning. The symptoms are not due to the direct physiological effects of a substance (e.g., a drug of abuse, a medication) or a general medical condition (e.g., hypothyroidism).

The symptoms are not better accounted for by Bereavement, i.e., after the loss of a loved one, the symptoms persist for longer than 2 months, or are characterized by marked functional impairment, morbid preoccupation with worthlessness, suicidal ideation, psychotic symptoms, or psychomotor retardation.

B. Criteria for Manic Episode

A manic episode is a distinct period of abnormally and persistently elevated, expansive, or irritable mood, lasting at least one week (or any duration, if hospitalization is necessary).

During the period of mood disturbance, three (or more) of the following symptoms have persisted (four if the mood is only irritable) and have been present to a significant degree:

(1) inflated self-esteem or grandiosity (2) decreased need for sleep (e.g., feels rested after only 3 hours of sleep)

(3) more talkative than usual or pressure to keep talking (4) flight of ideas or subjective experience that thoughts are racing (5) distractibility (i.e., attention too easily drawn to unimportant or irrelevant external stimuli)

(6) increase in goal-directed activity (either socially, at work or school, or sexually) or psychomotor agitation (7) excessive involvement in pleasurable activities that have a high potential for painful consequences (e.g., engaging in unrestrained buying sprees, sexual indiscretions, or foolish business investments)

The symptoms do not meet criteria for a Mixed Episode. The mood disturbance is sufficiently severe to cause marked impairment in occupational functioning or in usual social activities or relationships with others, or to necessitate hospitalization to prevent harm to self or others, or there are psychotic features. The symptoms are not due to the direct physiological effects of a substance (e.g., a drug of abuse, a medication, or other treatment) or a general medical condition (e.g., hyperthyroidism).

C. Criteria for Mixed Episode

A mixed episode occurs when the criteria are met both for a Manic Episode and for a Major Depressive Episode (except for duration) nearly every day during at least a 1-week period. The mood disturbance is sufficiently severe to cause marked impairment in occupational functioning or in usual social activities or relationships with others, or to necessitate hospitalization to prevent harm to self or others, or there are psychotic features.

The symptoms are not due to the direct physiological effects of a substance (e.g., a drug of abuse, a medication, or other treatment) or a general medical condition (e.g., hyperthyroidism).

D. Criterion A of SZ

See above.

E. Types of SD

The type of SD may be may be specifiable, as either Bipolar Type, if the disturbance includes a Manic or a Mixed Episode (or a Manic or a Mixed Episode and Major Depressive Episodes), or Depressive Type, if the disturbance only includes Major Depressive Episodes.

F. Associated Features

Features associated with SD include Learning Problems, Hypoactivity, Psychotic, Euphoric Mood, Depressed Mood, Somatic/Sexual Dysfunction, Hyperactivity, Guilt/Obsession, Odd/Eccentric/Suspicious Personality, Anxious/Fearful/Dependent Personality, and Dramatic/Erratic/Antisocial Personality.

Schizotypal Personality Disorder (SPD)

Diagnostic Criteria for SPD

A diagnosis of SPD under the criteria of the DSM-IV is generally based on a pervasive pattern of social and interpersonal deficits marked by acute discomfort with, and reduced capacity for, close relationships as well as by cognitive or perceptual distortions and eccentricities of behavior, beginning by early adulthood and present in a variety of contexts, as indicated by five (or more) of the following:

(1) ideas of reference (excluding delusions of reference)

(2) odd beliefs or magical thinking that influences behavior and is (3) inconsistent with subcultural norms (e.g., superstitiousness, belief in clairvoyance, telepathy, or "sixth sense;" in children and adolescents, bizarre fantasies or preoccupations)

(4) unusual perceptual experiences, including bodily illusions (5) odd thinking and speech (e.g., vague, circumstantial, metaphorical, overelaborate, or stereotyped)

(6) suspiciousness or paranoid ideation (7) inappropriate or constricted affect (8) behavior or appearance that is odd, eccentric, or peculiar (9) lack of close friends or confidants other than first-degree relatives

(10) excessive social anxiety that does not diminish with familiarity and tends to be associated with paranoid fears rather than negative judgments about self SPD is diagnosed if the symptoms do not occur exclusively during the course of SZ, a Mood Disorder With Psychotic Features, another Psychotic Disorder, or a Pervasive Developmental Disorder, and the disturbance is not due to the direct physiological effects of a substance (e.g., a drug of abuse, a medication) or a general medical condition.

Associated features of SPD include Depressed Mood and Odd/Eccentric/Suspicious Personality.

Bipolar Disorder (BD) (Diagnostic Criteria: Bipolar I, Bipolar II)

Also known as manic-depression or manic-depressive disorder. This condition is characterized by mood that alternates between two emotional extremes, or poles: the sadness of depression and the euphoria of mania (see symptoms of mania below).

Between these emotional swings, there are periods when a person's mood is quite normal. When a person is in the depressed phase of bipolar illness, he or she will have the same symptoms as those found in major depressive disorder. The depressive episodes can often be severe. While in a manic phase, a person experiences mood that is extremely elevated, expansive, or irritable. Mania can seriously impair one's normal judgment. When manic, a person is prone towards reckless and inappropriate behavior such as engaging in wild spending sprees or having promiscuous sex. He or she may not be able to realize the harm of his/her behavior and may even lose touch with reality.

There are two types of bipolar disorder:

Bipolar I Disorder is diagnosed when a person has had at least one manic or mixed episode, often along with a major depressive episode. It affects equal numbers of men and women in approximately 0.4% to 1.6% of the population. Bipolar II Disorder is diagnosed when a person has had a major depressive episode along with at least one hypomanic episode. It affects more women than men in about 0.5% of the population.

People with bipolar disorder experience a wide range of feelings depending on the phase of the illness is present. During a phase of depression, a person will have many of the symptoms of a major depressive episode. He or she may have despondent mood, a loss of energy, feelings of worthlessness or guilt, or problems with concentration. Thoughts of suicide are not uncommon. In fact, 10% to 15% of those with bipolar disorder may die by suicide. If the depression is severe, a person may need to be hospitalized for his or her own safety. For those who go through a phase of hypomania, the experience usually feels quite good. A person's mood and spirit lightens, he or she will be more outgoing and notice more energy and enhanced self-esteem. Lots of ideas come with ease and a person may feel compelled towards greater activity and productivity. A person in a hypomanic phase may also feel more powerful and omnipotent.

The manic phase is the most extreme part of bipolar disorder. A person becomes euphoric, ideas come much too fast, and concentration is nearly impossible. Anger, irritability, fear, and a sense of being out of control are overwhelming. A person's judgment is impaired, and he or she may behave recklessly without a sense of consequence. Some people lose touch with reality and experience delusions and hallucinations. When this happens, people often need to be hospitalized for their own safety. If a person with bipolar disorder experiences a severe manic episode, he or she may be abusive to children, spouses, or engage in other violent behaviors. There may also be problems with attendance and performance at school or work, as well as significant difficulties in personal relationships.

The cycles of bipolar disorder may be different for each person. Oftentimes a person may first experience depression. Then depression may be replaced with manic symptoms and the cycle between depression and mania may continue for days, weeks, or months. Between phases of depression and mania some people return to their normal mood. Some others have several periods of either depression or mania. Still others may experience several bouts of depression with infrequent phases of hypomania, or repeated manic episodes with occasional depressive periods. A portion of people, roughly 10% to 20% may only experience mania, while others can have both depression and mania at the same time.

For at least 90% of those who have bipolar disorder the condition is recurrent. They will experience future symptoms of the cycles of mania and depression. Approximately 60%-70% of manic episodes may happen just before or after a depressive episode, and this pattern may happen in a particular way for each person. Most people return to a regular level of functioning between episodes, while some (about 20%-30%) may continue to have some problems with mood stability and social and occupational functioning.

Bipolar I disorder affects equal numbers of males and females, however there does appear to be a gender difference in the onset of the illness. Females are more likely to experience a first episode of depression, while males tend to have a first episode that is manic. Women who have bipolar I or II disorder and who have children may be at a higher risk of experiencing bipolar episodes within several months of giving birth.

A first episode of mania is most likely to occur when a person is in his/her teens or twenties. If a person develops bipolar disorder for the first time after 40 years of age, he or she should be evaluated for the possibility of a medical illness or substance use.

People who have immediate relatives with bipolar I disorder have a higher risk of developing a mood disorder themselves. For these people the rate of developing bipolar II disorder or major depression is 4%-24% and bipolar I disorder is 1%-5%.

Of adolescents who have recurrent major depressive episodes, about 10%-15% of them will likely develop bipolar disorder.

Diagnostic Criteria of Bipolar I Disorder

Summarized from the *Diagnostic and Statistical Manual of Mental Disorders—Fourth Edition*

A. A person experiences a current or recent episode that is manic, hypomanic, mixed, or depressed.

1. To be a manic episode, for at least one week a person's mood must be out of the ordinary and continuously heightened, exaggerated, or irritable.

2. At least three of the following seven symptoms have been significant and enduring. If the mood is only irritable, then four symptoms are required.

a. Self-esteem is excessive or grandiose.
  b. The need for sleep is greatly reduced.
  c. Talks much more than usual.
  d. Thoughts and ideas are continuous and without a pattern or focus.
  e. Easily distracted by unimportant things.
  f. An increase in purposeful activity or productivity, or behaving and feeling agitated.
  g. Reckless participation in enjoyable activities that create a high risk for negative consequences (e.g., extensive spending sprees, sexual promiscuity).

3. The persons' symptoms do not indicate a mixed episode.

4. The person's symptoms are a cause of great distress or difficulty in functioning at home, work, or other important areas. Or, the symptoms require the person to be hospitalized to protect the person from harming himself/herself or others. Or, the symptoms include psychotic features (hallucinations, delusions).

5. The person's symptoms are not caused by substance use (e.g., alcohol, drugs, medication), or a medical disorder.

B. Unless this is a first single manic episode there has been at least one manic, mixed, hypomanic, or depressive episode.

1. For a major depressive episode a person must have experienced at least five of the nine symptoms below for the same two weeks or more, for most of the time almost every day, and this is a change from his/her prior level of functioning. One of the symptoms must be either (a) depressed mood, or (b) loss of interest.

a. Depressed mood. For children and adolescents, this may be irritable mood.
  b. A significantly reduced level of interest or pleasure in most or all activities.
  c. A considerable loss or gain of weight (e.g., 5% or more change of weight in a month when not dieting). This may also be an increase or decrease in appetite. For children, they may not gain an expected amount of weight.

d. Difficulty falling or staying asleep (insomnia), or sleeping more than usual (hypersomnia).

e. Behavior that is agitated or slowed down. Others should be able to observe this.

f. Feeling fatigued, or diminished energy.

g. Thoughts of worthlessness or extreme guilt (not about being ill).

h. Ability to think, concentrate, or make decisions is reduced.

i. Frequent thoughts of death or suicide (with or without a specific plan), or attempt of suicide.

2. The persons' symptoms do not indicate a mixed episode.

3. The person's symptoms are a cause of great distress or difficulty in functioning at home, work, or other important areas.

4. The person's symptoms are not caused by substance use (e.g., alcohol, drugs, medication), or a medical disorder.

5. The person's symptoms are not due to normal grief or bereavement over the death of a loved one, they continue for more than two months, or they include great difficulty in functioning, frequent thoughts of worthlessness, thoughts of suicide, symptoms that are psychotic, or behavior that is slowed down (psychomotor retardation).

C. Another disorder does not better explain the episode.

Diagnostic Criteria of Bipolar II Disorder

Summarized from the *Diagnostic and Statistical Manual of Mental Disorders—Fourth Edition*

A. The person currently has, or in the past has had at least one major depressive episode:

1. For a major depressive episode a person must have experienced at least five of the nine symptoms below for the same two weeks or more, for most of the time almost every day, and this is a change from his/her prior level of functioning. One of the symptoms must be either (a) depressed mood, or (b) loss of interest.

a. Depressed mood. For children and adolescents, this may be irritable mood.

b. A significantly reduced level of interest or pleasure in most or all activities.

c. A considerable loss or gain of weight (e.g., 5% or more change of weight in a month when not dieting). This may also be an increase or decrease in appetite. For children, they may not gain an expected amount of weight.

d. Difficulty falling or staying asleep (insomnia), or sleeping more than usual (hypersomnia).

e. Behavior that is agitated or slowed down. Others should be able to observe this.

f. Feeling fatigued, or diminished energy.

g. Thoughts of worthlessness or extreme guilt (not about being ill).

h. Ability to think, concentrate, or make decisions is reduced.

i. Frequent thoughts of death or suicide (with or without a specific plan), or attempt of suicide.

2. The persons' symptoms do not indicate a mixed episode.

3. The person's symptoms are a cause of great distress or difficulty in functioning at home, work, or other important areas.

4. The person's symptoms are not caused by substance use (e.g., alcohol, drugs, medication), or a medical disorder.

5. The person's symptoms are not due to normal grief or bereavement over the death of a loved one, they continue for more than two months, or they include great difficulty in functioning, frequent thoughts of worthlessness, thoughts of suicide, symptoms that are psychotic, or behavior that is slowed down (psychomotor retardation).

B. The person currently has, or in the past has had at least one hypomanic episode:

1. For a hypomanic episode a person's mood must be out of the ordinary and continuously heightened, exaggerated, or irritable for at least four days.

2. At least three of the following seven symptoms have been significant and enduring. If the mood is only irritable, then four symptoms are required.

a. Self-esteem is excessive or grandiose.

b. The need for sleep is greatly reduced.

c. Talks much more than usual.

d. Thoughts and ideas are continuous and without a pattern or focus.

e. Easily distracted by unimportant things.

f. An increase in purposeful activity or productivity, or behaving and feeling agitated.

g. Reckless participation in enjoyable activities that create a high risk for negative consequences (e.g., extensive spending sprees, sexual promiscuity).

3. The episode is a substantial change for the person and uncharacteristic of his or her usual functioning.

4. The changes of functioning and mood can be observed by others.

5. The person's symptoms are NOT severe enough to cause difficulty in functioning at home, work, or other important areas. Also, the symptoms neither require the person to be hospitalized, nor are there any psychotic features.

6. The person's symptoms are not caused by substance use (e.g., alcohol, drugs, medication), or a medical disorder. C. The person has never experienced a manic or mixed episode. D. Another disorder does not better explain the episode. E. The symptoms are a cause of great distress or difficulty in functioning at home, work, or other important areas.

Endophenotypes in SZ and BD

A number of endophenotypes, i.e., intermediate phenotypes, that may more closely reflect biological mechanisms behind SZ and DB, have been suggested, such as prepulse inhibition, structural abnormalities evident in MRI scans, specific domains of cognition (e.g., executive function), fine motor performance, working memory, etc.

Endophenotypes can also include clinical manifestations such as hallucinations, paranoia, mania, depression, obsessive-compulsive symptoms, etc., as well as response or lack of response to drugs and comorbidity for substance and alcohol abuse.

See, e.g., Kendler et al., Am J Psychiatry 152(5):749-54 (1995); Gottesman and Gould, Am J Psychiatry 160(4):636-45 (2003); Cadenhead, Psychiatric Clinics of North America. 25(4):837-53 (2002); Gottesman and Gould, American Journal of Psychiatry. 160(4):636-45 (2003); Heinrichs, Neuroscience & Biobehavioral Reviews. 28(4):379-94 (2004); and Zobel and Maier, Nervenarzt. 75(3):205-14 (2004).

There is now evidence that some candidate genes that were identified using DSM-IV type categorical definitions for "affected" individuals may influence specific endophenotypes, see, e.g., Baker et al., Biol Psychiatry 58(1):23-31 (2005); Cannon et al., Arch Gen Psychiatry 62(11):1205-13 (2005); Gothelf et al., Nat Neurosci 8(11):1500-2 (2005); Hallmayer et al., Am J Hum Genet 77(3):468-76 (2005); Callicott et al., Proc Natl Acad Sci USA 102(24):8627-32 (2005); Gornick et al., J Autism Dev Disord 1-8 (2005). Thus, the methods described herein can be used to associate haplotypes of HPCAL1 or SV2C with specific endophenotypes.

Current Treatment of SZ, SD, SPD, BD

Subjects with SZ typically require acute treatment for psychotic exacerbations, and long-term treatment including maintenance and prophylactic strategies to sustain symptom improvement and prevent recurrence of psychosis. Subjects with schizoaffective disorder experience the symptoms of both SZ and affective disorder (manic and/or depressive), thus require the specific treatments for each disorder. Subjects with SPD sometimes require medication for acute psychotic episodes but are often treated using psychosocial methods. The methods described herein can include the administration of one or more accepted or experimental treatment modalities to a person identified as at risk of developing SZ, SD, SPD or BD, based on the presence of a haplotype associated with SZ or BD. Currently accepted treatments presently include both pharmacologic and psychosocial management, and occasionally electroconvulsive therapy (ECT).

Standard pharmacologic therapies for SZ and SD include the administration of one or more antipsychotic medications, which are typically antagonists acting at postsynaptic $D_2$ dopamine receptors in the brain. Antipsychotic medications include conventional, or first generation, antipsychotic agents, which are sometimes referred to as neuroleptics because of their neurologic side effects, and second generation antipsychotic agents, which are less likely to exhibit neuroleptic effects and have been termed atypical antipsychotics.

In some embodiments, the methods described herein include the administration of one or more antipsychotic medications to a person identified by a method described herein as being at risk of developing SZ or BD. Antipsychotic medications substantially reduce the risk of relapse in the stable phase of illness. In some embodiments, the methods include the administration of a first generation antipsychotic medication at a dose that is around the "extrapyramidal symptom (EPS) threshold" (i.e., the dose that will induce extrapyramidal side effects, e.g., bradykinesia, rigidity, or dyskinesia, with minimal rigidity detectable on physical examination, and/or a second-generation antipsychotics at a dose that is therapeutic, yet below the EPS threshold.

Standard pharmacologic therapies for SD also include the administration of a combination of antidepressant, and anti-anxiety medication. Suitable antidepressants include serotonergic antidepressants, e.g., fluoxetine or trazodone. Suitable anxiolytics include benzodiazepines, e.g., lorazepam, clonazepam. Lithium can also be administered. Thus, in some embodiments, the methods can include the administration of one or more antidepressant and/or anti-anxiety medications to a person identified as at risk of developing SZ or BD.

The methods can also include psychosocial and rehabilitation interventions, e.g., interventions that are generally accepted as therapeutically beneficial, e.g., cognitive-behavioral therapy for treatment-resistant positive psychotic symptoms; supportive, problem-solving, educationally oriented psychotherapy; family therapy and education programs aimed at helping patients and their families understand the patient's illness, reduce stress, and enhance coping capabilities; social and living skills training; supported employment programs; and/or the provision of supervised residential living arrangements.

Currently accepted treatments for SZ are described in greater detail in the *Practice Guideline for the Treatment of Patients With Schizophrenia American Psychiatric Association*, Second Edition, American Psychiatric Association, 2004, which is incorporated herein by reference in its entirety.

Currently accepted treatments for BD are described in detail in *American Psychiatric Association Practice Guideline for the Treatment of Patients With Bipolar Disorder*, Second Edition, American Psychiatric Association, 2002 which is incorporated herein by reference in its entirety.

Methods of Determining Treatment Regimens and Methods of Treating SZ, SPD, SD, or BD As described herein, the presence of haplotypes described herein has been correlated with an increased risk of developing or having SZ or BD. Thus, the new methods can also include selecting a treatment regimen for a subject determined to be at risk for developing SZ or BD, based upon the absence or presence of a haplotype associated with SZ or BD as described herein. The determination of a treatment regimen can also be based upon the absence or presence of other risk factors associated with SZ or BD, e.g., as described herein. Therefore, the methods of the invention can include selecting a treatment regimen for a subject having one or more risk factors for SZ or BD, and having a haplotype described herein. The methods can also include administering a treatment regimen to a subject having, or at risk of developing, SZ or BD to thereby treat, prevent or delay further progression of the disease. A treatment regimen can include the administration of antipsychotic medications to a subject identified as at risk of developing SZ or BD before the onset of any psychotic episodes.

As used herein, the term "treat" or "treatment" is defined as the application or administration of a treatment regimen, e.g., a therapeutic agent or modality, to a subject, e.g., a patient. The subject can be a patient having SZ or BD, a symptom of SZ or BD or at risk of developing (i.e., a predisposition toward) SZ or BD. The treatment can be to cure, heal, alleviate, relieve, alter, remedy, ameliorate, palliate, improve or affect SZ or BD, the symptoms of SZ or BD or the predisposition toward SZ or BD.

The methods of the invention, e.g., methods of determining a treatment regimen and methods of treatment or prevention of SZ or BD, can further include the step of monitoring the subject, e.g., for a change (e.g., an increase or decrease) in one or more of the diagnostic criteria for SZ or BD listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

The methods can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response genotype. In a preferred embodiment, a treatment for SZ or BD can be evaluated by administering the same treatment or combinations or treatments to a subject having SZ, SPD, SD or BD and a haplotype as described herein and to a subject that has SZ or BD but does not have a haplotype as described herein. The effects of the treatment or combination of treatments on each of these subjects can be used to determine if a treatment or combination of treatments is particularly effective on a sub-group of subjects having SZ, SPD, SD or BD. In other embodiments, various treatments or combinations of treatments can be evaluated by administering two different treatments or combinations of treatments to at least two different subjects having SZ, SPD, SD or BD and a haplotype as described herein. Such methods can be used to determine if a particular treatment or combination of treatments is more effective than others in treating this subset of SZ, SPD, SD and/or or BD patients.

Various treatment regimens are known for treating SZ, e.g., as described herein.

Pharmacogenomics

With regards to both prophylactic and therapeutic methods of treatment of SZ or BD, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market. See, for example, Eichelbaum et al., Clin. Exp. Pharmacol. Physiol. 23:983-985 (1996) and Linder et al., Clin. Chem. 43:254-266 (1997). Specifically, as used herein, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a cytotoxic agent or combination of cytotoxic agents, to a patient, as a means of treating or preventing SZ or BD.

In one embodiment, a physician or clinician may consider applying knowledge obtained in relevant pharmacogenomics studies, e.g., using a method described herein, when determining whether to administer a pharmaceutical composition, e.g., an antipsychotic agent or a combination of antipsychotic agents, to a subject. In another embodiment, a physician or clinician may consider applying such knowledge when determining the dosage, e.g., amount per treatment or frequency of treatments, of a treatment, e.g., a antipsychotic agent or combination of antipsychotic agents, administered to a patient.

As one example, a physician or clinician may determine (or have determined, e.g., by a laboratory) the haplotype of a subject as described herein, and optionally one or more other markers associated with SZ or BD, of one or a group of subjects who may be participating in a clinical trial, wherein the subjects have SZ, SPD, SD, or BD, and the clinical trial is designed to test the efficacy of a pharmaceutical composition, e.g., an antipsychotic or combination of antipsychotic agents, and wherein the physician or clinician attempts to correlate the genotypes of the subjects with their response to the pharmaceutical composition.

As another example, information regarding a haplotype associated with an increased risk of SZ or BD as described herein, can be used to stratify or select a subject population for a clinical trial. The information can, in some embodiments, be used to stratify individuals that may exhibit a toxic response to a treatment from those that will not. In other cases, the information can be used to separate those that will be non-responders from those who will be responders. The haplotypes described herein can be used in pharmacogenomics-based design and manage the conduct of a clinical trial, e.g., as described in U.S. Pat. Pub. No. 2003/0108938.

As another example, information regarding a haplotype associated with an increased risk of SZ or BD, as described herein, can be used to stratify or select human cells or cell lines for drug testing purposes. Human cells are useful for studying the effect of a polymorphism on physiological function, and for identifying and/or evaluating potential therapeutic agents for the treatment of SZ, SPD, SD, or BD, e.g., anti-psychotics. Thus the methods can include performing the present methods on genetic material from a cell line. The information can, in some embodiments, be used to separate cells that respond particular drugs from those that do not respond, e.g. which cells show altered second messenger signaling.

Theranostics

Also included herein are compositions and methods for the identification and treatment of subjects who have an increased risk of SZ, SPD, SD, or BD, such that a theranostic approach can be taken to test such individuals to determine the effectiveness of a particular therapeutic intervention (e.g., a pharmaceutical or non-pharmaceutical intervention as described herein) and to alter the intervention to 1) reduce the risk of developing adverse outcomes and 2) enhance the effectiveness of the intervention. Thus, in addition to diagnosing or confirming the predisposition to SZ or BD, the methods and compositions described herein also provide a means of optimizing the treatment of a subject having such a disorder. Provided herein is a theranostic approach to treating and preventing SZ or BD, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a haplotype as described herein and any measurable or quantifiable parameter relating to the outcome of the treatment, e.g., efficacy (the results of which may be binary (i.e., yes and no) as well as along a continuum), side-effect profile (e.g., weight gain, metabolic dysfunction, lipid dysfunction, movement disorders, or extrapyramidal symptoms), treatment maintenance and discontinuation rates, return to work status, hospitalizations, suicidality, total healthcare cost, social functioning scales, response to non-pharmacological treatments, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, high treatment maintenance/low discontinuation rates, good return to work status, low hospitalizations, low suicidality, low total healthcare cost, high social function scale, favorable response to non-pharmacological treatments, and/or acceptable dose response curves) and a selected haplotype can influence treatment such that the treatment is recommended or selected for a subject having the selected haplotype.

Kits

Also within the scope of the invention are kits comprising a probe that hybridizes with a region of human chromosome as described herein and can be used to detect a polymorphism described herein. The kit can include one or more other elements including: instructions for use; and other reagents, e.g., a label, or an agent useful for attaching a label to the probe. Instructions for use can include instructions for diagnostic applications of the probe for assessing risk of SZ in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome as described herein, e.g., a labeled probe as described herein.

The kit can also include one or more additional probes that hybridize to the same chromosome, e.g., chromosome 2, 5 or 10, or another chromosome or portion thereof that can have an abnormality associated with risk for SZ or BD. For example, the additional probe or probes can be: a probe that hybridizes to human chromosome 22q11-12 or a portion thereof, (e.g., a probe that detects a sequence associated with SZ or BD in this region of chromosome 22), or probes that hybridize to all or a portion of 22q12.3 (e.g., near D22S283), 22q11.2, 22q11.2, 22q11-q13, 1q42.1, 1q42.1, 1q21-q22, 2p, 2q, 3p25, 4p, 4q, 5q11.2-q13.3, 6p23, 6p23, 6q13-q26, 7q, 8p12-21, 8q, 9p, 10p15-p13 (e.g., near D10S189), 10q22.3, 11q14-q21, 12q24, 13q34, 13q32, 14q32.3, 15q15, 16p, 17q, 18p, 18q, 19p. 20p, 21q, Xq, and/or the X/Y pseudoautosomal region. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Databases

Also provided herein are databases that include a list of polymorphisms as described herein, and wherein the list is largely or entirely limited to polymorphisms identified as useful in performing genetic diagnosis of or determination of susceptibility to SZ or BD as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular haplotype and the information regarding the subject, e.g., to detect correlations between a haplotype and a particular endophenotype, or treatment response.

Engineered Cells

Also provided herein are engineered cells that harbor one or more polymorphism described herein, e.g., one or more polymorphisms that constitute a haplotype associated with SZ or BD. Such cells are useful for studying the effect of a polymorphism on physiological function, and for identifying and/or evaluating potential therapeutic agents for the treatment of SZ, SPD, SD, or BD, e.g., anti-psychotics.

As one example, included herein are cells in which one of the various alleles of the genes described herein has be re-created that is associated with an increased risk of SZ or BD. Methods are known in the art for generating cells, e.g., by homologous recombination between the endogenous gene and an exogenous DNA molecule introduced into a cell, e.g., a cell of an animal. In some embodiments, the cells can be used to generate transgenic animals using methods known in the art.

The cells are preferably human cells, e.g., neuronal type cells, in which an endogenous gene has been altered to include a polymorphism as described herein. Techniques such as targeted homologous recombinations, can be used to insert the heterologous DNA as described in, e.g., Chappel, U.S. Pat. No. 5,272,071; WO 91/06667, published in May 16, 1991.

The invention is further described in the following examples, which do not limit the scope of the invention described in the claims.

EXAMPLES

Example 1

Transmission Disequilibrium Testing (TDT) for HPCAL1

Samples from 241 families, comprising 1029 individuals, each having multiple affected siblings were obtained from NIMH. Self-description of heritage was as follows: African-American for SZ, 29 families; European/Mediterranean for SZ, 131 families; European/Mediterranean for BD, 81 families. DSM-IIIR or DSM-IV criteria were compiled for all subjects by researchers at Columbia University, Harvard University and Washington University. Detailed information on ascertainment, diagnosis and informed consent has been previously provided by these groups (Cloninger et al., (1998) Am. J. Med. Genet. 81, 275-281; Faraone et al., (1998) Am. J. Med. Genet. 81, 290-295; Kaufmann et al., (1998) Am. J. Med. Genet. 81, 282-289).

SNPs were genotyped by ABI ASSAYS-ON-DEMAND™ genotyping kits using the conditions suggested by the supplier (5 μl reactions in 384-well plates, containing 4.5 ng genomic DNA). PCR products were analyzed using the ABI Prism 7900HT Sequence Detection System. In cases where a reaction failed (<3% of total), or the results were not consistent with Mendelian inheritance (<0.5% of total), a second reaction was carried out to resolve discrepancies.

Transmission disequilibrium (TDT) analysis was performed to test for the possibility of allelic association in the presence linkage (Laird and Lange, (2006) Nat. Rev. Genet. 7, 385-394). TDT analysis was performed using TRANSMIT (Version 2.5.2), which uses a robust variance estimate that allows for multiple affected members in each family, in effect, treating families, rather than siblings, as independent entities (Clayton, (1999) Am. J. Hum. Genet. 65, 1170-1177; Martin et al., (2003) Am. J. Hum. Genet. 73, 1016-1026). Alleles were aggregated so as to prevent elevation of $X^2$ values that can arise due to expectations for rare haplotypes. The resulting global $X^2$ analyses estimate the significance of the transmission distribution for all alleles combined, with rare haplotypes being treated as a single group. Similarly, $X^2$ values for transmission of individual alleles, with one degree of freedom, were determined by TRANSMIT. To arrive at conservative estimates of Type I error probabilities for TDT analysis, 100,000 bootstrap replicates in TRANSMIT were used to determine empirical probabilities. This approach is particularly conservative, as it randomly samples a single affected individual for each family.

In total, 11 SNPs in HPCAL1 (listed in Table A) were tested for association with SZ and BD in NIMH family samples. Preferential transmissions of higher risk genetic variants in HPCAL1 and decreased transmissions of protective variants in HPCAL1 for both SZ and BD are documented in Tables 1 through 3.

TABLE 1

HPCAL1 TDT analysis for Caucasian Schizophrenia Families

| SNP or haplotype | Preferentially transmitted (under-transmitted) | Chi square (df) | P value (bootstrap replication) |
|---|---|---|---|
| rs887873 | A | 4.3 (1) | 0.046 |
| rs11893459 | C | 7.9 (1) | 0.001 |
| rs11694643 | C | 4.1 (1) | 0.043 |
| rs887973 - rs11893459 | Global | 10.9 (3) | 0.012 |
|  | A - C | 7.0 (1) | 0.004 |
|  | (G-T) | 7.3 (1) | 0.005 |
| rs11893459 - rs2270299 | Global | 7.1 (3) | 0.036 |
|  | C - C | 4.0 (1) | 0.033 |
|  | (T-C) | 4.1 (1) | 0.024 |
| rs11694643 - rs3732120 | Global | 6.3 (3) | 0.023 |
|  | C-C | 4.5 (1) | 0.038 |
|  | (T-C) | 6.3 (1) | 0.010 |
| rs6755271 - rs887973 - rs11893459 | Global | 17.8 (7) | 0.005 |
|  | G-A-C | 4.3 (1) | 0.039 |
|  | (G-G-T) | 7.75 (1) | 0.001 |
| rs887973 - rs11893459 - rs2270299 | Global | 11.4 (7) | 0.021 |
|  | G-C-C | 7.7 (1) | 0.002 |
|  | (G-T-C) | 3.9 (1) | 0.026 |
| rs11893459 - rs2270299 - | Global | 15.2 (7) | 0.004 |
|  | C-T-G | 5.0 (1) | 0.013 |
|  | (T-C-G) | 4.0 (1) | 0.016 |
| rs11694643 - rs3732120 - | Global | 7.4 (6) | 0.050 |
|  | C-C-G | 4.5 (1) | 0.023 |
|  | (T-C-A) | 4.1 (1) | 0.022 |

TABLE 2

HPCAL1 TDT analysis for African American Schizophrenia Families

| SNP or haplotype | Preferentially transmitted (under-transmitted) | Chi square (df) | P value (bootstrap replication) |
|---|---|---|---|
| rs1808315 | C | 3.2 (1) | 0.020 |
| rs2270299 - rs1808315 | Global | 4.1 (3) | 0.130 (NS) |
|  | C-G | 3.0 (1) | 0.020 |

TABLE 3

HPCAL1 TDT analysis for Caucasian Bipolar Disorder Families

| SNP or haplotype | Preferentially transmitted (under-transmitted) | Chi square (df) | P value (bootstrap replication) |
|---|---|---|---|
| rs11893459 | C | 11.1 (1) | 0.003 |
| rs887973 - rs11893459 | Global | 10.8 (3) | 0.017 |
|  | (T-C) | 9.9 (1) | 0.005 |

As can be seen, there is preferential transmission of alleles for several markers and haplotypes. In addition to the results reported in Tables 1-3, highly significant results are seen for the broad disease definition including both SZ and BP (n=212 Caucasian families) particularly for marker rs11893459 which displays preferential transmission of the rs11893459 (C) allele (chi square=22.2 [1 df]; bootstrap P value=$1\times10^{-6}$) as well as preferential transmission of several haplotypes involving this SNP marker.

Example 2

Transmission Disequilibrium Testing (TDT) for SV2C

TDT analysis was performed on the SV2C gene as described above in Example 1. In total, 8 SNPs (listed in Table A) in SV2C were tested for association with SZ and BD in NIMH family samples. Preferential transmissions of higher risk genetic variants in SV2C and decreased transmissions of protective variants in SV2C for both SZ and BD are documented in Tables 4 through 6.

TABLE 4

SV2C TDT analysis for Caucasian Schizophrenia Families

| SNP or haplotype | Preferentially transmitted (under-transmitted) | Chi square (df) | P value (bootstrap replication) |
|---|---|---|---|
| rs889189 | G | 5.7 (1) | 0.0070 |
| rs889189 (males only) | G | 1.9 (1) | 0.083 (NS) |
| rs889189 (females only) | G | 4.9 (1) | 0.0280 |
| rs6453211 (males only) | C | 3.2 (1) | 0.0520 |
| rs4704298 (males only) | C | 3.6 (1) | 0.0390 |
| rs6453211- rs4704298 (males only) | Global | 4.3 (2) | 0.076 (NS) |
|  | C - C | 3.2 (1) | 0.056 (NS) |
|  | (T-T) | 3.7 (1) | 0.0380 |

TABLE 5

SV2C TDT analysis for African American Schizophrenia Families

| SNP or haplotype | Preferentially transmitted (under-transmitted) | Chi square (df) | P value (bootstrap replication) |
|---|---|---|---|
| rs889189 | A | 4.8 (1) | 0.0060 |
| rs2270927 (males only) | C = Thr | 3.2 (1) | 0.0100 |
| rs31244 | A = Asn | 5.8 (1) | 0.0050 |
| rs889189 - rs736005 | Global | 6.8 (3) | 0.0007 |
|  | A-C | 4.8 (1) | 0.0002 |
|  | (G-G) | 4.5 (1) | 0.0001 |
| rs4704298 - rs1501926 | Global | 4.7 (3) | 0.081 (NS) |
|  | (T-T) | 4.5 (1) | 0.0002 |

TABLE 5-continued

SV2C TDT analysis for African American Schizophrenia Families

| SNP or haplotype | Preferentially transmitted (under-transmitted) | Chi square (df) | P value (bootstrap replication) |
|---|---|---|---|
| rs4704298 - rs1501926 (males | Global (T-T) | 7.4 (3) 4.7 (1) | 0.0050 0.0001 |
| rs11960621 - rs2270927 (males | Global G-C (G-G) | 5.6 (3) 2.9 (1) 5.0 (1) | 0.0440 0.023 0.0160 |
| rs6453211 - rs4704298 - rs1501926 | Global (T-T-T) | 7.7 (5) 4.2 (1) | 0.087 (NS) 0.0035 |
| rs11960621 - rs2270927 - rs31244 | Global G-C-A | 7.2 (4) 3.4 (1) | 0.1513 (NS) 0.0058 |

TABLE 6

SV2C TDT analysis for Caucasian Bipolar Disorder Families

| SNP or haplotype | Preferentially transmitted (under-transmitted) | Chi square (df) | P value (bootstrap replication) |
|---|---|---|---|
| rs889189 (females only) | A | 3.8 (1) | 0.042 |
| rs889189 - rs736005 | Global (G-G) | 5.0 (3) 3.8 (1) | 0.089 (NS) 0.017 |
| rs889189 - rs736005 (females only) | Global A-C (G-G) | 7.2 (3) 4.7 (1) 4.9 (1) | 0.035 0.017 0.029 |
| rs889189 - rs736005 - rs6453211 | Global A-C-T | 10.2 (7) 2.5 (1) | 0.072 (NS) 0.049 |
| rs889189 - rs736005 - rs6453211 | Global A-C-T (G-G-C) | 10.8 (7) 3.5 (1) 4.5 (1) | 0.071 (NS) 0.004 0.021 |

As can be seen in Tables 4-6, there is preferential transmission of alleles for several markers and haplotypes. Markers near the 5' end of SV2C show altered transmission for Caucasian SZ and BD families. Additionally, the 5' SNP rs889189, and haplotypes involving this SNP, show disease-type specific differences in allelic transmission for females in Caucasian families. More centrally located markers show stronger distortion in transmission frequencies for male Caucasians. Interestingly, 5' markers and haplotypes are involved in African American SZ families as well, and these families show the same pattern as Caucasians SZ families in that centrally located markers are relatively more important in males. The two nonsynonymous coding variants [rs2270927 (C), corresponding the amino acid threonine (Thr), and rs31244(A) corresponding to the amino acid asparagine (Asn)] are preferentially transmitted to affected individuals in African American SZ families. These variants are more prevalent in African Americans.

Example 3

Case/Control Analysis for HPCAL1

Allele frequencies for the HPCAL1 SNPs listed in Table A were determined for probands from the NIMH families described in Example 1 (Cases). Allele frequencies in cases were compared to those in ethnically matched controls (Controls; n=100 CA, and 100 AA DNAs obtained from the Coriell Institute for Medical Research). Genotyping was as specified in Example 1.

TABLE 7

HPCAL1 Case/Control Analysis for Schizophrenia and Bipolar Disorder

| SNP or haplotype (Disease, Population) | Allele | Odds ratio | Chi square | P |
|---|---|---|---|---|
| rs11893459 (BD, CA) | C | 1.84 | 4.2 | 0.04 |
| rs17882379 (SZ, AA) | C | 2.35 | 4.5 | 0.03 |
| rs1808315 (SZ, AA) | G | 2.05 | 3.9 | 0.05 |

As determined using haploview software (from broad.mit.edu/mpg/haploview/) (Barrett et al., Bioinformatics. 21:263-265 (2005)), there were three significant differences in allele and haplotype frequencies in Case/Control comparisons for both Caucasian and African American schizophrenics with a family history of disease (Table 7).

Example 4

Case/Control Analysis for SV2C

Allele frequencies for the SV2C SNPs listed in Table A were determined for probands from the NIMH families described in Example 1 (Cases). Allele frequencies in cases were compared to those in ethnically matched controls (Controls; n=100 CA, and 100 AA DNAs obtained from the Coriell Institute for Medical Research). Genotyping was as specified in Example 1, and genetic analysis was as specified in Example 4.

As can be seen in Tables 8 and 9, there are numerous examples of alleles and haplotypes for SV2C that are associated with either increased risk of SZ (odds ratio>1) or decreased risk of SZ (odds ratio<1). For SV2C, there were no significant Case/Control results for the small sample of CA Bipolar Disorder probands tested.

TABLE 8

SV2C Case/Control Analysis for Caucasian Schizophrenics

| SNP or haplotype | Allele | Odds ratio | Chi square | P |
|---|---|---|---|---|
| rs1501926 | C | 1.60 | 5.9 | 0.015 |
| rs4704298 - rs1501926 | C-C | 1.54 | 4.2 | 0.042 |
|  | T-T | 0.60 | 4.0 | 0.045 |
| rs1501926 - rs1196062 | C-G | 1.48 | 3.8 | 0.050 |
|  | T-A | 0.50 | 5.2 | 0.023 |
| rs6453211 - rs4704298 - rs1501926 | C-C-C | 1.58 | 4.2 | 0.040 |
|  | T-T-T | 0.53 | 4.0 | 0.045 |
| rs1501926 - rs1196062 - rs2270927 | C-G-G | 1.62 | 5.2 | 0.023 |
|  | T-A-G | 0.54 | 3.7 | 0.053 |
| rs1501926 - rs1196062 - rs2270927-rs31244 | C-G-G-G | 1.61 | 5.0 | 0.025 |

TABLE 9

SV2C Case/Control Analysis for African American Schizophrenics

| SNP or haplotype | Allele | Odds ratio | Chi square | P |
|---|---|---|---|---|
| rs736005 - 6453211 | C-T | 2.0 | 5.0 | 0.026 |
|  | C-C | 0.52 | 4.1 | 0.043 |
| rs2270927 - rs31244 | G-G | 0.46 | 4.8 | 0.029 |
| rs889189 - rs736005 - | A-C-T | 2.0 | 4.9 | 0.026 |
| rs1196062 - rs2270927 - rs31244 | G-G-G | 0.55 | 3.7 | 0.054 |

Example 5

Altered Pharmacogenomic Response in SZ Related to HPCAL1 and SV2C SNPs

The Clinical Antipsychotic Trials of Intervention Effectiveness (CATIE), a large federally funded clinical trial designed to assess the efficacy of antipsychotics in a real world setting, is a valuable resource for determining the role of genes in drug response (Stroup et al., Schizophr. Bull. 29:15-31 (2003); Lieberman et al., N. Engl. J. Med. 353: 1209-1223 (2005)). As part of the CATIE trial SNP genotyping was performed for roughly half of the trial participants (Sullivan et al., Mol. Psychiatry 13:570-584 (2008)). When combined with clinical drug response data, the genotyping data make possible a reduction to practice for the current invention as it relates to pharmacogenomic applications.

The design of the CATIE study has been described in detail by others (Stroup et al., Schizophr. Bull. 29:15-31 (2003); Lieberman et al., N. Engl. J. Med. 353:1209-1223 (2005)). Briefly, 1460 subjects were randomly assigned one of several antipsychotics and those who did not respond or chose to quit their current medication were re-randomized to another drug. A total of 738 subjects consented to provide DNA for genetic study. Details regarding SNP genotyping and quality control have been recently published (Sullivan et al., Mol. Psychiatry 13:570-584 (2008)).

Genotype and phenotype data for the CATIE trial were made available to qualified researchers through The NIMH Center for Collaborative Genetic Studies on Mental Disorders. For reduction to practice, we evaluated data for 417 patients with schizophrenia self reported as having exclusively European ancestry. This same patient population was described in a recent study by Sullivan and coworkers, which confirmed that there is no hidden stratification in the sample (Sullivan et al., Mol. Psychiatry 13:570-584 (2008)).

For each drug, response and side effect rates were compared between the genotype categories using HelixTree software (Version 6.4.1; Golden Helix, Bozeman, Mont.). To generate a P value, HelixTree calculates analysis of deviance (a likelihood ratio statistic) that compares the observed contingency table vs. an expected contingency table created with all the possible variations of the genetic model.

To assess drug response, the last observation for each patient in treatment Phase 1 of the trial was used as a primary assessment of efficacy. The standard FDA registration trial definition of response of >20% decrease in Positive and Negative Syndrome Scale (PANSS Total Score) was used to assign subjects to a response category. Individuals having composite ordinal effectiveness outcome (COMPEFF) scores of 1 of 2, indicating efficacy, were combined as were those with scores of 3 or 4, indicating lack of efficacy (Davis et al., Schizophr. Bull. 29:73-80 (2003)). The side effects category consisted of individuals discontinued for safety concerns (COMPEFF score 5).

As can be seen in Tables 10 and 11, there are numerous examples of SNP-based genotypes for SV2C and HPCAL1 (in linkage disequilibrium with those listed in Table A) that predict altered response to antipsychotic drugs. As indicated by the odds ratios of >1.0, certain SNP-based genotypes for SV2C and HPCAL1 are associated with increased response to specific drugs (Table 10) or increased levels of side effects (Table 11). The tables report odds ratios relative to the baseline values (sample not segmented by genotype) and relative to values for the low scoring, mutually exclusive genotype(s).

TABLE 10

Improved Drug Response Predicted by HPCAL1 and SV2C SNPs

| Drug | Gene | SNP | P | Genotype (contributing allele) | Response frequency | OR vs. baseline | OR vs. Low | Table A Marker (D') |
|---|---|---|---|---|---|---|---|---|
| Overall Response | SV2C | rs12522597 | 0.009 | G/G, A/G (G) | 0.46 | 1.18 | 1.99 | rs736005 (0.78) |
| Overall Response | SV2C | rs4704297 | 0.012 | C/C, C/G (C) | 0.46 | 1.18 | 2.09 | rs4704298 (1.0) |
| perphenazine | SV2C | rs6453205 | 0.023 | C/C (C) | 0.7 | 2.43 | 3.36 | rs736005 (0.86) |
| quetiapine | HPCAL1 | rs11679891 | 0.037 | C/C (C) | 0.6 | 3.05 | 3.86 | rs6755271 (0.92) |
| quetiapine | SV2C | rs4610441 | 0.017 | C/C (C) | 0.6 | 3.05 | 4.06 | rs736005 (1.0) |
| quetiapine | SV2C | rs10474464 | 0.037 | C/C (C) | 0.6 | 3.05 | 4.06 | rs736005 (1.0) |
| quetiapine | SV2C | rs12152728 | 0.037 | C/C (C) | 0.5 | 2.03 | 2.70 | rs736005 (1.0) |
| quetiapine | SV2C | rs10064352 | 0.046 | T/T (T) | 0.6 | 3.05 | 3.67 | rs736005 (1.0) |
| risperidone | SV2C | rs4704297 | 0.025 | C/C, C/G (C) | 0.45 | 1.39 | 3.49 | rs4704298 (1.0) |
| ziprasidone | SV2C | rs12522597 | 0.007 | G/G, A/G (G) | 0.55 | 1.49 | 9.89 | rs736005 (0.78) |

TABLE 11

Increased Side Effects Predicted by HPCAL1 and SV2C SNPs

| Drug Name | Gene | SNP | P | Genotype (contributing allele) | Frequency Study ending side effects | OR vs. baseline | OR vs. Low | Table A Marker (D') |
|---|---|---|---|---|---|---|---|---|
| Overall Response | HPCAL1 | rs11679891 | 0.049 | A/C, C/C (C) | 0.21 | 1.13 | 1.78 | rs6755271 (0.92) |
| Overall Response | SV2C | rs12655684 | 0.014 | T/T (T) | 0.5 | 4.26 | 4.56 | rs4704298 (1.0) |
| olanzapine | HPCAL1 | rs7566866 | 0.011 | C/T, T/T (T) | 0.5 | 3.00 | 4.00 | rs2270299 (1.0) |
| olanzapine | SV2C | rs17651115 | 0.002 | G/G (G) | 0.43 | 2.26 | 4.63 | rs736005 (1.0) |
| olanzapine | SV2C | rs1895391 | 0.024 | C/T, T/T (T) | 0.3 | 1.29 | 4.33 | rs736005 (1.0) |
| olanzapine | SV2C | rs12657276 | 0.0007 | G/G (G) | 0.48 | 2.77 | 5.67 | rs736005 (.78) |
| olanzapine | SV2C | rs4610441 | 0.009 | C/C (C) | 0.5 | 3.00 | 4.26 | rs736005 (1.0) |
| olanzapine | SV2C | rs10474464 | 0.035 | C/C (C) | 0.54 | 3.52 | 4.70 | rs736005 (1.0) |
| olanzapine | SV2C | rs12152728 | 0.029 | C/C (C) | 0.5 | 3.00 | 3.76 | rs736005 (1.0) |
| olanzapine | SV2C | rs10064352 | 0.044 | T/T (T) | 0.46 | 2.56 | 3.20 | rs736005 (1.0) |
| olanzapine | SV2C | rs12655684 | 0.031 | T/T (T) | 0.75 | 9.00 | 10.04 | rs4704298 (1.0) |
| perphenazine | HPCAL1 | rs11679891 | 0.005 | C/C, A/C (C) | 0.19 | 1.44 | >10 | rs6755271 (0.92) |
| perphenazine | HPCAL1 | rs13033617 | 0.040 | C/C (C) | 0.27 | 2.27 | 3.74 | rs887973 (0.84) |
| risperidone | SV2C | rs1895391 | 0.041 | C/C (C) | 0.23 | 2.19 | 3.97 | rs736005 (1.0) |
| risperidone | SV2C | rs10474464 | 0.040 | T/T (T) | 0.21 | 1.95 | 3.53 | rs736005 (1.0) |
| risperidone | SV2C | rs12152728 | 0.037 | G/G (G) | 0.21 | 1.95 | 3.53 | rs736005 (1.0) |
| risperidone | SV2C | rs10064352 | 0.037 | C/C (C) | 0.21 | 1.95 | 3.53 | rs736005 (1.0) |
| risperidone | SV2C | rs6874435 | 0.028 | A/G, G/G (G) | 0.24 | 2.32 | 4.20 | rs2270927 (1.0) and rs31244 (1.0) |
| risperidone | SV2C | rs2270927 | 0.039 | G/G (G) | 1 | >10 | >10 | rs2270927 |
| ziprasidone | HPCAL1 | rs7571627 | 0.036 | T/T (T) | 0.33 | 1.56 | 4.98 | rs4668676 (0.78) |
| ziprasidone | SV2C | rs246812 | 0.017 | A/A (A) | 0.5 | 3.17 | 6.14 | rs2270927 (1.0) and rs31244 (1.0) |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE A

SNP Markers Used for TDT and Association Analyses

| Gene Name | Marker | Chromosome | Position (bp)** |
|---|---|---|---|
| HPCAL1 | rs4668676 | 2p25.1 | 10,356,072 |
| HPCAL1 | rs6714483 | 2p25.1 | 10,362,983 |
| HPCAL1 | rs17882379 | 2p25.1 | 10,394,102 |
| HPCAL1 | rs6755271 | 2p25.1 | 10,427,491 |
| HPCAL1 | rs887973 | 2p25.1 | 10,431,133 |
| HPCAL1 | rs11893459 | 2p25.1 | 10,443,439 |
| HPCAL1 | rs2270299 | 2p25.1 | 10,453,937 |
| HPCAL1 | rs1808315 | 2p25.1 | 10,460,455 |
| HPCAL1 | rs11694643 | 2p25.1 | 10,470,378 |
| HPCAL1 | rs3732120 | 2p25.1 | 10,479,913 |
| HPCAL1 | rs12692407 | 2p25.1 | 10,491,404 |
| SV2C | rs889189 | 5q13.3 | 75,459,441 |
| SV2C | rs736005 | 5q13.3 | 75,483,802 |
| SV2C | rs6453211 | 5q13.3 | 75,549,151 |
| SV2C | rs4704298 | 5q13.3 | 75,549,821 |
| SV2C | rs1501926 | 5q13.3 | 75,569,146 |
| SV2C | rs11960621 | 5q13.3 | 75,603,754 |
| SV2C | rs2270927 | 5q13.3 | 75,627,466 |
| SV2C | rs31244 | 5q13.3 | 75,630,499 |

**The position shown is relative to NCBI Genome Build 36.3.

TABLE B

SNPs in Linkage Disequilibrium with SNPs in Table A

| Chrom. | TABLE A SNP | Location (BP)** | SNP In LD | Location (BP)** | D' |
|---|---|---|---|---|---|
| 2 | rs4668676 | 10356072 | rs2192670 | 10357807 | 0.96 |
| 2 | rs4668676 | 10356072 | rs2884208 | 10358438 | 1 |
| 2 | rs4668676 | 10356072 | rs6432091 | 10363132 | 0.959 |
| 2 | rs6755271 | 10427491 | rs10929656 | 10428308 | 1 |
| 2 | rs6755271 | 10427491 | rs10929657 | 10428377 | 1 |
| 2 | rs6755271 | 10427491 | rs16856158 | 10428770 | 1 |
| 2 | rs6755271 | 10427491 | rs7563637 | 10429833 | 0.882 |
| 2 | rs6755271 | 10427491 | rs7563835 | 10430031 | 0.913 |
| 2 | rs6755271 | 10427491 | rs11684791 | 10430315 | 0.875 |
| 2 | rs6755271 | 10427491 | rs2041741 | 10431747 | 1 |
| 2 | rs6755271 | 10427491 | rs2016436 | 10432457 | 0.917 |
| 2 | rs6755271 | 10427491 | rs6742677 | 10432992 | 0.891 |
| 2 | rs6755271 | 10427491 | rs13388873 | 10433398 | 0.915 |
| 2 | rs6755271 | 10427491 | rs12466783 | 10434928 | 1 |
| 2 | rs6755271 | 10427491 | rs12692405 | 10434944 | 0.831 |
| 2 | rs6755271 | 10427491 | rs7559838 | 10435003 | 0.797 |
| 2 | rs6755271 | 10427491 | rs7560149 | 10435286 | 0.797 |
| 2 | rs6755271 | 10427491 | rs16856174 | 10435581 | 1 |
| 2 | rs6755271 | 10427491 | rs11679891 | 10435606 | 0.929 |
| 2 | rs6755271 | 10427491 | rs13015407 | 10436147 | 1 |
| 2 | rs6755271 | 10427491 | rs13021624 | 10436897 | 1 |
| 2 | rs6755271 | 10427491 | rs12477018 | 10437298 | 1 |
| 2 | rs6755271 | 10427491 | rs13009040 | 10437474 | 1 |
| 2 | rs6755271 | 10427491 | rs6721270 | 10438577 | 1 |
| 2 | rs6755271 | 10427491 | rs6721291 | 10438623 | 0.828 |
| 2 | rs6755271 | 10427491 | rs10198351 | 10442231 | 0.797 |
| 2 | rs6755271 | 10427491 | rs13033617 | 10443831 | 0.792 |
| 2 | rs6755271 | 10427491 | rs7566866 | 10451297 | 0.8 |
| 2 | rs6755271 | 10427491 | rs4669582 | 10452103 | 0.8 |
| 2 | rs6755271 | 10427491 | rs11681700 | 10454798 | 0.8 |
| 2 | rs887973 | 10431133 | rs2041741 | 10431747 | 1 |
| 2 | rs887973 | 10431133 | rs2016436 | 10432457 | 0.962 |
| 2 | rs887973 | 10431133 | rs2016640 | 10432593 | 1 |
| 2 | rs887973 | 10431133 | rs6742677 | 10432992 | 0.96 |
| 2 | rs887973 | 10431133 | rs10198139 | 10433221 | 0.966 |
| 2 | rs887973 | 10431133 | rs13388873 | 10433398 | 1 |
| 2 | rs887973 | 10431133 | rs9967756 | 10433880 | 0.966 |
| 2 | rs887973 | 10431133 | rs12466783 | 10434928 | 1 |
| 2 | rs887973 | 10431133 | rs7559838 | 10435003 | 0.812 |
| 2 | rs887973 | 10431133 | rs7560149 | 10435286 | 0.812 |
| 2 | rs887973 | 10431133 | rs16856174 | 10435581 | 1 |
| 2 | rs887973 | 10431133 | rs11685619 | 10435679 | 1 |
| 2 | rs887973 | 10431133 | rs13015407 | 10436147 | 1 |
| 2 | rs887973 | 10431133 | rs13021624 | 10436897 | 1 |
| 2 | rs887973 | 10431133 | rs12477018 | 10437298 | 1 |
| 2 | rs887973 | 10431133 | rs13009040 | 10437474 | 1 |
| 2 | rs887973 | 10431133 | rs6721270 | 10438577 | 1 |
| 2 | rs887973 | 10431133 | rs6721291 | 10438623 | 0.847 |
| 2 | rs887973 | 10431133 | rs13033617 | 10443831 | 0.848 |
| 2 | rs887973 | 10431133 | rs11884075 | 10444799 | 0.857 |
| 2 | rs2270299 | 10453937 | rs2270300 | 10454179 | 1 |
| 2 | rs2270299 | 10453937 | rs2270301 | 10454205 | 1 |
| 2 | rs2270299 | 10453937 | rs2270302 | 10454469 | 1 |
| 2 | rs2270299 | 10453937 | rs2270303 | 10454574 | 1 |
| 2 | rs2270299 | 10453937 | rs7594864 | 10454767 | 1 |
| 2 | rs2270299 | 10453937 | rs11681700 | 10454798 | 1 |
| 2 | rs2270299 | 10453937 | rs11676661 | 10454913 | 1 |
| 2 | rs2270299 | 10453937 | rs3771148 | 10455324 | 1 |
| 2 | rs2270299 | 10453937 | rs3771147 | 10455365 | 0.938 |
| 2 | rs2270299 | 10453937 | rs3771145 | 10456420 | 1 |
| 2 | rs2270299 | 10453937 | rs4668685 | 10457837 | 0.953 |
| 2 | rs2270299 | 10453937 | rs3771138 | 10462091 | 0.892 |
| 2 | rs2270299 | 10453937 | rs3755264 | 10463687 | 0.892 |
| 2 | rs2270299 | 10453937 | rs3771134 | 10464611 | 0.895 |
| 2 | rs2270299 | 10453937 | rs12467741 | 10465558 | 0.813 |
| 2 | rs2270299 | 10453937 | rs7603352 | 10466464 | 0.921 |
| 2 | rs2270299 | 10453937 | rs3821200 | 10471379 | 0.881 |
| 2 | rs2270299 | 10453937 | rs3821199 | 10472665 | 0.921 |
| 2 | rs2270299 | 10453937 | rs3771122 | 10473227 | 1 |
| 2 | rs2270299 | 10453937 | rs9917369 | 10479498 | 0.891 |
| 2 | rs2270299 | 10453937 | rs3771120 | 10482376 | 0.896 |
| 2 | rs2270299 | 10453937 | rs3821197 | 10482541 | 0.896 |
| 2 | rs4668676 | 10356072 | rs7571627 | 10352165 | 0.797 |
| 2 | rs4668676 | 10356072 | rs6432089 | 10353849 | 0.859 |
| 2 | rs6755271 | 10427491 | rs4669579 | 10422029 | 1 |
| 2 | rs887973 | 10431133 | rs4669579 | 10422029 | 1 |
| 2 | rs2270299 | 10453937 | rs4669579 | 10422029 | 1 |
| 2 | rs6755271 | 10427491 | rs11888000 | 10425893 | 1 |
| 2 | rs887973 | 10431133 | rs11888000 | 10425893 | 0.889 |
| 2 | rs6755271 | 10427491 | rs6753925 | 10426215 | 1 |
| 2 | rs887973 | 10431133 | rs6753925 | 10426215 | 0.958 |
| 2 | rs887973 | 10431133 | rs10929656 | 10428308 | 1 |
| 2 | rs2270299 | 10453937 | rs10929656 | 10428308 | 1 |
| 2 | rs887973 | 10431133 | rs10929657 | 10428377 | 1 |
| 2 | rs2270299 | 10453937 | rs10929657 | 10428377 | 1 |
| 2 | rs887973 | 10431133 | rs7563637 | 10429833 | 0.929 |
| 2 | rs887973 | 10431133 | rs7563835 | 10430031 | 1 |
| 2 | rs887973 | 10431133 | rs7561055 | 10430067 | 1 |
| 2 | rs887973 | 10431133 | rs7573168 | 10430127 | 1 |
| 2 | rs887973 | 10431133 | rs11684791 | 10430315 | 1 |
| 2 | rs887973 | 10431133 | rs867953 | 10430468 | 1 |
| 2 | rs887973 | 10431133 | rs2357549 | 10430823 | 1 |
| 2 | rs2270299 | 10453937 | rs16856165 | 10434729 | 1 |
| 2 | rs2270299 | 10453937 | rs13392890 | 10434759 | 1 |
| 2 | rs2270299 | 10453937 | rs12466783 | 10434928 | 1 |
| 2 | rs2270299 | 10453937 | rs10490727 | 10434959 | 1 |
| 2 | rs2270299 | 10453937 | rs16856174 | 10435581 | 1 |
| 2 | rs2270299 | 10453937 | rs11685619 | 10435679 | 1 |
| 2 | rs2270299 | 10453937 | rs12477018 | 10437298 | 1 |
| 2 | rs2270299 | 10453937 | rs11888704 | 10447776 | 0.826 |
| 2 | rs2270299 | 10453937 | rs7608670 | 10450259 | 1 |
| 2 | rs2270299 | 10453937 | rs7582990 | 10450320 | 1 |
| 2 | rs2270299 | 10453937 | rs10929659 | 10450419 | 1 |
| 2 | rs2270299 | 10453937 | rs7582930 | 10450924 | 1 |
| 2 | rs2270299 | 10453937 | rs7580561 | 10451280 | 1 |
| 2 | rs2270299 | 10453937 | rs7566866 | 10451297 | 1 |
| 2 | rs2270299 | 10453937 | rs7583465 | 10451372 | 1 |
| 2 | rs2270299 | 10453937 | rs17434886 | 10451826 | 1 |
| 2 | rs2270299 | 10453937 | rs4669582 | 10452103 | 1 |
| 2 | rs2270299 | 10453937 | rs7584151 | 10452165 | 1 |
| 2 | rs2270299 | 10453937 | rs10169634 | 10452806 | 1 |
| 2 | rs2270299 | 10453937 | rs11686947 | 10452932 | 1 |
| 2 | rs2270299 | 10453937 | rs16856193 | 10453273 | 1 |
| 2 | rs4668676 | 10356072 | rs7571627 | 10352165 | 0.797 |
| 2 | rs4668676 | 10356072 | rs6432089 | 10353849 | 0.859 |
| 2 | rs6755271 | 10427491 | rs4669579 | 10422029 | 1 |
| 2 | rs887973 | 10431133 | rs4669579 | 10422029 | 1 |
| 2 | rs2270299 | 10453937 | rs4669579 | 10422029 | 1 |
| 2 | rs6755271 | 10427491 | rs11888000 | 10425893 | 1 |
| 2 | rs887973 | 10431133 | rs11888000 | 10425893 | 0.889 |
| 2 | rs6755271 | 10427491 | rs6753925 | 10426215 | 1 |
| 2 | rs887973 | 10431133 | rs6753925 | 10426215 | 0.958 |
| 2 | rs887973 | 10431133 | rs10929656 | 10428308 | 1 |
| 2 | rs2270299 | 10453937 | rs10929656 | 10428308 | 1 |
| 2 | rs887973 | 10431133 | rs10929657 | 10428377 | 1 |
| 2 | rs2270299 | 10453937 | rs10929657 | 10428377 | 1 |
| 2 | rs887973 | 10431133 | rs7563637 | 10429833 | 0.929 |
| 2 | rs887973 | 10431133 | rs7563835 | 10430031 | 1 |
| 2 | rs887973 | 10431133 | rs7561055 | 10430067 | 1 |
| 2 | rs887973 | 10431133 | rs7573168 | 10430127 | 1 |
| 2 | rs887973 | 10431133 | rs11684791 | 10430315 | 1 |
| 2 | rs887973 | 10431133 | rs867953 | 10430468 | 1 |
| 2 | rs887973 | 10431133 | rs2357549 | 10430823 | 1 |
| 2 | rs2270299 | 10453937 | rs16856165 | 10434729 | 1 |
| 2 | rs2270299 | 10453937 | rs13392890 | 10434759 | 1 |
| 2 | rs2270299 | 10453937 | rs12466783 | 10434928 | 1 |
| 2 | rs2270299 | 10453937 | rs10490727 | 10434959 | 1 |
| 2 | rs2270299 | 10453937 | rs16856174 | 10435581 | 1 |
| 2 | rs2270299 | 10453937 | rs11685619 | 10435679 | 1 |
| 2 | rs2270299 | 10453937 | rs12477018 | 10437298 | 1 |
| 2 | rs2270299 | 10453937 | rs11888704 | 10447776 | 0.826 |
| 2 | rs2270299 | 10453937 | rs7608670 | 10450259 | 1 |
| 2 | rs2270299 | 10453937 | rs7582990 | 10450320 | 1 |
| 2 | rs2270299 | 10453937 | rs10929659 | 10450419 | 1 |
| 2 | rs2270299 | 10453937 | rs7582930 | 10450924 | 1 |
| 2 | rs2270299 | 10453937 | rs7580561 | 10451280 | 1 |
| 2 | rs2270299 | 10453937 | rs7566866 | 10451297 | 1 |
| 2 | rs2270299 | 10453937 | rs7583465 | 10451372 | 1 |
| 2 | rs2270299 | 10453937 | rs17434886 | 10451826 | 1 |
| 2 | rs2270299 | 10453937 | rs4669582 | 10452103 | 1 |

TABLE B-continued

SNPs in Linkage Disequilibrium with SNPs in Table A

| Chrom. | TABLE A SNP | Location (BP)** | SNP In LD | Location (BP)** | D' |
|---|---|---|---|---|---|
| 2 | rs2270299 | 10453937 | rs7584151 | 10452165 | 1 |
| 2 | rs2270299 | 10453937 | rs10169634 | 10452806 | 1 |
| 2 | rs2270299 | 10453937 | rs11686947 | 10452932 | 1 |
| 2 | rs2270299 | 10453937 | rs16856193 | 10453273 | 1 |
| 5 | rs4704298 | 75549821 | rs31244 | 75630499 | 1 |
| 5 | rs4704298 | 75549821 | rs246815 | 75634932 | 1 |
| 5 | rs4704298 | 75549821 | rs246814 | 75634964 | 1 |
| 5 | rs4704298 | 75549821 | rs246813 | 75635361 | 1 |
| 5 | rs4704298 | 75549821 | rs2972843 | 75638147 | 1 |
| 5 | rs4704298 | 75549821 | rs2937747 | 75638305 | 1 |
| 5 | rs4704298 | 75549821 | rs2937746 | 75638459 | 1 |
| 5 | rs4704298 | 75549821 | rs2913266 | 75638972 | 1 |
| 5 | rs4704298 | 75549821 | rs2972846 | 75640778 | 1 |
| 5 | rs4704298 | 75549821 | rs2913262 | 75641646 | 1 |
| 5 | rs4704298 | 75549821 | rs2937743 | 75641934 | 1 |
| 5 | rs4704298 | 75549821 | rs2972847 | 75643740 | 1 |
| 5 | rs4704298 | 75549821 | rs2913260 | 75644923 | 1 |
| 5 | rs4704298 | 75549821 | rs1863919 | 75646103 | 1 |
| 5 | rs4704298 | 75549821 | rs2972848 | 75647064 | 1 |
| 5 | rs4704298 | 75549821 | rs1971744 | 75647353 | 1 |
| 5 | rs4704298 | 75549821 | rs2972850 | 75647761 | 1 |
| 5 | rs4704298 | 75549821 | rs2937741 | 75647994 | 1 |
| 5 | rs4704298 | 75549821 | rs2913258 | 75648018 | 1 |
| 5 | rs4704298 | 75549821 | rs2913257 | 75648088 | 1 |
| 5 | rs4704298 | 75549821 | rs1469387 | 75651212 | 1 |
| 5 | rs4704298 | 75549821 | rs2972853 | 75651715 | 1 |
| 5 | rs4704298 | 75549821 | rs2937740 | | 1 |
| 5 | rs2270927 | 75627466 | rs31243 | 75630116 | 1 |
| 5 | rs2270927 | 75627466 | rs31244 | 75630499 | 1 |
| 5 | rs2270927 | 75627466 | rs246815 | 75634932 | 1 |
| 5 | rs2270927 | 75627466 | rs246814 | 75634964 | 1 |
| 5 | rs2270927 | 75627466 | rs246813 | 75635361 | 1 |
| 5 | rs2270927 | 75627466 | rs246812 | 75635907 | 1 |
| 5 | rs2270927 | 75627466 | rs246811 | 75636685 | 0.796 |
| 5 | rs2270927 | 75627466 | rs2972843 | 75638147 | 0.862 |
| 5 | rs2270927 | 75627466 | rs2937747 | 75638305 | 0.862 |
| 5 | rs2270927 | 75627466 | rs2937746 | 75638459 | 0.862 |
| 5 | rs2270927 | 75627466 | rs2913266 | 75638972 | 0.862 |
| 5 | rs2270927 | 75627466 | rs2972844 | 75640607 | 1 |
| 5 | rs2270927 | 75627466 | rs2972845 | 75640623 | 1 |
| 5 | rs2270927 | 75627466 | rs2972846 | 75640778 | 0.862 |
| 5 | rs2270927 | 75627466 | rs2913262 | 75641646 | 0.862 |
| 5 | rs2270927 | 75627466 | rs2937743 | 75641934 | 0.862 |
| 5 | rs2270927 | 75627466 | rs4703705 | 75642464 | 1 |
| 5 | rs2270927 | 75627466 | rs2972847 | 75643740 | 0.862 |
| 5 | rs2270927 | 75627466 | rs2913260 | 75644923 | 1 |
| 5 | rs2270927 | 75627466 | rs3909796 | 75645442 | 1 |
| 5 | rs2270927 | 75627466 | rs1863919 | 75646103 | 0.862 |
| 5 | rs2270927 | 75627466 | rs2972848 | 75647064 | 0.862 |
| 5 | rs2270927 | 75627466 | rs1971744 | 75647353 | 0.862 |
| 5 | rs2270927 | 75627466 | rs2972850 | 75647761 | 0.862 |
| 5 | rs2270927 | 75627466 | rs2937741 | 75647994 | 0.862 |
| 5 | rs2270927 | 75627466 | rs2913258 | 75648018 | 0.862 |
| 5 | rs2270927 | 75627466 | rs2913257 | 75648088 | 0.862 |
| 5 | rs2270927 | 75627466 | rs1834886 | 75648632 | 1 |
| 5 | rs2270927 | 75627466 | rs2012412 | 75650863 | 1 |
| 5 | rs2270927 | 75627466 | rs1469387 | 75651212 | 0.862 |
| 5 | rs2270927 | 75627466 | rs2972853 | 75651715 | 1 |
| 5 | rs2270927 | 75627466 | rs3733860 | | 1 |
| 5 | rs2270927 | 75627466 | rs3733861 | | 1 |
| 5 | rs2270927 | 75627466 | rs2937740 | | 1 |
| 5 | rs2270927 | 75627466 | rs6892721 | | 1 |
| 5 | rs31244 | 75630499 | rs246815 | 75634932 | 1 |
| 5 | rs31244 | 75630499 | rs246814 | 75634964 | 1 |
| 5 | rs31244 | 75630499 | rs246813 | 75635361 | 1 |
| 5 | rs31244 | 75630499 | rs246812 | 75635907 | 1 |
| 5 | rs31244 | 75630499 | rs2972843 | 75638147 | 1 |
| 5 | rs31244 | 75630499 | rs2937747 | 75638305 | 1 |
| 5 | rs31244 | 75630499 | rs2937746 | 75638459 | 1 |
| 5 | rs31244 | 75630499 | rs2913266 | 75638972 | 1 |
| 5 | rs31244 | 75630499 | rs2972844 | 75640607 | 1 |
| 5 | rs31244 | 75630499 | rs2972845 | 75640623 | 1 |
| 5 | rs31244 | 75630499 | rs2972846 | 75640778 | 1 |
| 5 | rs31244 | 75630499 | rs2913262 | 75641646 | 1 |
| 5 | rs31244 | 75630499 | rs2937743 | 75641934 | 1 |
| 5 | rs31244 | 75630499 | rs4703705 | 75642464 | 1 |
| 5 | rs31244 | 75630499 | rs2972847 | 75643740 | 1 |
| 5 | rs31244 | 75630499 | rs2913261 | 75644749 | 1 |
| 5 | rs31244 | 75630499 | rs2913260 | 75644923 | 1 |
| 5 | rs31244 | 75630499 | rs3909796 | 75645442 | 1 |
| 5 | rs31244 | 75630499 | rs1863919 | 75646103 | 1 |
| 5 | rs31244 | 75630499 | rs2972848 | 75647064 | 1 |
| 5 | rs31244 | 75630499 | rs1971744 | 75647353 | 1 |
| 5 | rs31244 | 75630499 | rs2972850 | 75647761 | 1 |
| 5 | rs31244 | 75630499 | rs2937741 | 75647994 | 1 |
| 5 | rs31244 | 75630499 | rs2913258 | 75648018 | 1 |
| 5 | rs31244 | 75630499 | rs2913257 | 75648088 | 1 |
| 5 | rs31244 | 75630499 | rs1834886 | 75648632 | 1 |
| 5 | rs31244 | 75630499 | rs2012412 | 75650863 | 1 |
| 5 | rs31244 | 75630499 | rs1469387 | 75651212 | 1 |
| 5 | rs31244 | 75630499 | rs2972853 | 75651715 | 1 |
| 5 | rs31244 | 75630499 | rs2913254 | 75652555 | 1 |
| 5 | rs31244 | 75630499 | rs3733860 | | 1 |
| 5 | rs31244 | 75630499 | rs3733861 | | 1 |
| 5 | rs31244 | 75630499 | rs2937740 | | 1 |
| 5 | rs31244 | 75630499 | rs2913251 | | 1 |
| 5 | rs31244 | 75630499 | rs6892721 | | 1 |
| 5 | rs31244 | 75630499 | rs30205 | | 0.755 |
| 5 | rs31244 | 75630499 | rs1423103 | | 0.755 |
| 5 | rs736005 | 75483802 | rs2059157 | 75484439 | 1 |
| 5 | rs736005 | 75483802 | rs4299714 | 75484881 | 0.833 |
| 5 | rs736005 | 75483802 | rs1990976 | 75485317 | 1 |
| 5 | rs736005 | 75483802 | rs1559203 | 75485570 | 1 |
| 5 | rs736005 | 75483802 | rs6879305 | 75485883 | 0.833 |
| 5 | rs736005 | 75483802 | rs6898301 | 75486268 | 0.833 |
| 5 | rs736005 | 75483802 | rs6898618 | 75486452 | 0.83 |
| 5 | rs736005 | 75483802 | rs6889023 | 75486745 | 0.833 |
| 5 | rs736005 | 75483802 | rs6897128 | 75489276 | 0.833 |
| 5 | rs736005 | 75483802 | rs6897302 | 75489379 | 0.833 |
| 5 | rs736005 | 75483802 | rs10066377 | 75489779 | 1 |
| 5 | rs736005 | 75483802 | rs11955072 | 75490616 | 0.833 |
| 5 | rs736005 | 75483802 | rs6887093 | 75491007 | 1 |
| 5 | rs736005 | 75483802 | rs1895390 | 75491406 | 1 |
| 5 | rs736005 | 75483802 | rs12522618 | 75491695 | 1 |
| 5 | rs736005 | 75483802 | rs12657276 | 75493848 | 0.792 |
| 5 | rs736005 | 75483802 | rs4610441 | 75494157 | 1 |
| 5 | rs736005 | 75483802 | rs6453208 | 75500186 | 1 |
| 5 | rs736005 | 75483802 | rs12653182 | 75501263 | 1 |
| 5 | rs736005 | 75483802 | rs4704283 | 75506572 | 1 |
| 5 | rs736005 | 75483802 | rs1553325 | 75507473 | 1 |
| 5 | rs736005 | 75483802 | rs9293675 | 75510536 | 1 |
| 5 | rs736005 | 75483802 | rs10474464 | 75510677 | 1 |
| 5 | rs736005 | 75483802 | rs12152728 | 75510758 | 1 |
| 5 | rs736005 | 75483802 | rs10040232 | 75512957 | 1 |
| 5 | rs736005 | 75483802 | rs10064352 | 75512971 | 1 |
| 5 | rs736005 | 75483802 | rs7732173 | 75513419 | 1 |
| 5 | rs736005 | 75483802 | rs10514062 | 75513972 | 1 |
| 5 | rs736005 | 75483802 | rs2358531 | 75515542 | 1 |
| 5 | rs736005 | 75483802 | rs17651269 | 75518900 | 1 |
| 5 | rs736005 | 75483802 | rs1553323 | 75561255 | 1 |
| 5 | rs736005 | 75483802 | rs7722883 | 75565660 | 1 |
| 5 | rs736005 | 75483802 | rs7723272 | 75565920 | 1 |
| 5 | rs736005 | 75483802 | rs7722224 | 75565974 | 1 |
| 5 | rs736005 | 75483802 | rs11952839 | 75566885 | 1 |
| 5 | rs736005 | 75483802 | rs11952928 | 75567159 | 1 |
| 5 | rs736005 | 75483802 | rs11959221 | 75567188 | 1 |
| 5 | rs736005 | 75483802 | rs6865983 | 75569772 | 1 |
| 5 | rs736005 | 75483802 | rs16873285 | 75585993 | 1 |
| 5 | rs736005 | 75483802 | rs1995381 | 75606414 | 1 |
| 5 | rs736005 | 75483802 | rs2937748 | 75607788 | 1 |
| 5 | rs736005 | 75483802 | rs4352583 | 75612472 | 1 |
| 5 | rs736005 | 75483802 | rs4496693 | 75612485 | 0.83 |
| 5 | rs736005 | 75483802 | rs6876070 | 75614993 | 1 |
| 5 | rs736005 | 75483802 | rs7730153 | 75615518 | 1 |
| 5 | rs736005 | 75483802 | rs13188781 | 75616165 | 1 |
| 5 | rs736005 | 75483802 | rs2358712 | 75616443 | 1 |
| 5 | rs736005 | 75483802 | rs6453214 | 75620179 | 1 |
| 5 | rs736005 | 75483802 | rs10942765 | 75627080 | 1 |
| 5 | rs736005 | 75483802 | rs2270927 | 75627466 | 0.83 |
| 5 | rs736005 | 75483802 | rs31243 | 75630116 | 0.83 |

TABLE B-continued

SNPs in Linkage Disequilibrium with SNPs in Table A

| Chrom. | TABLE A SNP | Location (BP)** | SNP In LD | Location (BP)** | D' |
|---|---|---|---|---|---|
| 5 | rs736005 | 75483802 | rs31244 | 75630499 | 1 |
| 5 | rs736005 | 75483802 | rs246815 | 75634932 | 1 |
| 5 | rs736005 | 75483802 | rs246814 | 75634964 | 1 |
| 5 | rs736005 | 75483802 | rs246813 | 75635361 | 1 |
| 5 | rs736005 | 75483802 | rs2972843 | 75638147 | 1 |
| 5 | rs736005 | 75483802 | rs2937747 | 75638305 | 1 |
| 5 | rs736005 | 75483802 | rs2937746 | 75638459 | 1 |
| 5 | rs736005 | 75483802 | rs2913266 | 75638972 | 1 |
| 5 | rs736005 | 75483802 | rs2972846 | 75640778 | 1 |
| 5 | rs736005 | 75483802 | rs2913262 | 75641646 | 1 |
| 5 | rs736005 | 75483802 | rs2937743 | 75641934 | 1 |
| 5 | rs736005 | 75483802 | rs2972847 | 75643740 | 1 |
| 5 | rs736005 | 75483802 | rs2913260 | 75644923 | 1 |
| 5 | rs736005 | 75483802 | rs1863919 | 75646103 | 1 |
| 5 | rs736005 | 75483802 | rs2972848 | 75647064 | 1 |
| 5 | rs736005 | 75483802 | rs1971744 | 75647353 | 1 |
| 5 | rs736005 | 75483802 | rs2972850 | 75647761 | 1 |
| 5 | rs736005 | 75483802 | rs2937741 | 75647994 | 1 |
| 5 | rs736005 | 75483802 | rs2913258 | 75648018 | 1 |
| 5 | rs736005 | 75483802 | rs2913257 | 75648088 | 1 |
| 5 | rs736005 | 75483802 | rs1469387 | 75651212 | 1 |
| 5 | rs736005 | 75483802 | rs2972853 | 75651715 | 1 |
| 5 | rs736005 | 75483802 | rs2937740 | | 1 |
| 5 | rs4704298 | 75549821 | rs1553322 | 75560897 | 1 |
| 5 | rs4704298 | 75549821 | rs1553323 | 75561255 | 1 |
| 5 | rs4704298 | 75549821 | rs7722883 | 75565660 | 1 |
| 5 | rs4704298 | 75549821 | rs7723272 | 75565920 | 1 |
| 5 | rs4704298 | 75549821 | rs7722224 | 75565974 | 1 |
| 5 | rs4704298 | 75549821 | rs11952839 | 75566885 | 1 |
| 5 | rs4704298 | 75549821 | rs11952928 | 75567159 | 1 |
| 5 | rs4704298 | 75549821 | rs11959221 | 75567188 | 1 |
| 5 | rs4704298 | 75549821 | rs6865983 | 75569772 | 1 |
| 5 | rs4704298 | 75549821 | rs16873285 | 75585993 | 1 |
| 5 | rs4704298 | 75549821 | rs1995381 | 75606414 | 1 |
| 5 | rs4704298 | 75549821 | rs2937748 | 75607788 | 1 |
| 5 | rs4704298 | 75549821 | rs4352583 | 75612472 | 1 |
| 5 | rs4704298 | 75549821 | rs6876070 | 75614993 | 1 |
| 5 | rs4704298 | 75549821 | rs7730153 | 75615518 | 1 |
| 5 | rs4704298 | 75549821 | rs13188781 | 75616165 | 1 |
| 5 | rs4704298 | 75549821 | rs2358712 | 75616443 | 1 |
| 5 | rs4704298 | 75549821 | rs6453214 | 75620179 | 1 |
| 5 | rs4704298 | 75549821 | rs10942765 | 75627080 | 1 |
| 5 | rs31244 | 75630499 | rs28621 | 75417559 | 1 |
| 5 | rs31244 | 75630499 | rs258621 | 75427806 | 1 |
| 5 | rs31244 | 75630499 | rs187285 | 75428878 | 1 |
| 5 | rs31244 | 75630499 | rs183767 | 75428973 | 1 |
| 5 | rs31244 | 75630499 | rs2731735 | 75431992 | 1 |
| 5 | rs31244 | 75630499 | rs1501905 | 75433640 | 1 |
| 5 | rs736005 | 75483802 | rs17746675 | 75434347 | 1 |
| 5 | rs4704298 | 75549821 | rs17746675 | 75434347 | 1 |
| 5 | rs2270927 | 75627466 | rs17746675 | 75434347 | 1 |
| 5 | rs31244 | 75630499 | rs17746675 | 75434347 | 1 |
| 5 | rs31244 | 75630499 | rs258613 | 75435808 | 1 |
| 5 | rs2270927 | 75627466 | rs2112865 | 75465359 | 1 |
| 5 | rs31244 | 75630499 | rs2112865 | 75465359 | 1 |
| 5 | rs2270927 | 75627466 | rs7706479 | 75465738 | 1 |
| 5 | rs31244 | 75630499 | rs7706479 | 75465738 | 1 |
| 5 | rs736005 | 75483802 | rs12522597 | 75467455 | 0.784 |
| 5 | rs736005 | 75483802 | rs17650942 | 75468996 | 0.755 |
| 5 | rs736005 | 75483802 | rs13155330 | 75469259 | 1 |
| 5 | rs4704298 | 75549821 | rs13155330 | 75469259 | 1 |
| 5 | rs736005 | 75483802 | rs17565925 | 75469842 | 1 |
| 5 | rs4704298 | 75549821 | rs17565925 | 75469842 | 1 |
| 5 | rs736005 | 75483802 | rs17565946 | 75470086 | 1 |
| 5 | rs4704298 | 75549821 | rs17565946 | 75470086 | 1 |
| 5 | rs736005 | 75483802 | rs17565960 | 75471030 | 1 |
| 5 | rs4704298 | 75549821 | rs17565960 | 75471030 | 1 |
| 5 | rs736005 | 75483802 | rs10514060 | 75471101 | 1 |
| 5 | rs4704298 | 75549821 | rs10514060 | 75471101 | 1 |
| 5 | rs736005 | 75483802 | rs10514061 | 75471124 | 1 |
| 5 | rs4704298 | 75549821 | rs10514061 | 75471124 | 1 |
| 5 | rs736005 | 75483802 | rs7718358 | 75472047 | 0.755 |
| 5 | rs736005 | 75483802 | rs7701465 | 75472145 | 0.755 |
| 5 | rs736005 | 75483802 | rs6453203 | 75472467 | 0.852 |
| 5 | rs736005 | 75483802 | rs6860159 | 75473682 | 0.755 |
| 5 | rs736005 | 75483802 | rs6881418 | 75473912 | 0.755 |
| 5 | rs736005 | 75483802 | rs6859434 | 75473996 | 0.755 |
| 5 | rs736005 | 75483802 | rs10066177 | 75474180 | 1 |
| 5 | rs2270927 | 75627466 | rs10066177 | 75474180 | 1 |
| 5 | rs31244 | 75630499 | rs10066177 | 75474180 | 1 |
| 5 | rs736005 | 75483802 | rs13178459 | 75474224 | 0.755 |
| 5 | rs736005 | 75483802 | rs13174339 | 75474294 | 0.755 |
| 5 | rs736005 | 75483802 | rs6453204 | 75474956 | 1 |
| 5 | rs2270927 | 75627466 | rs6453204 | 75474956 | 1 |
| 5 | rs31244 | 75630499 | rs6453204 | 75474956 | 1 |
| 5 | rs736005 | 75483802 | rs6453205 | 75474978 | 0.869 |
| 5 | rs736005 | 75483802 | rs6453206 | 75475216 | 1 |
| 5 | rs736005 | 75483802 | rs17651115 | 75475886 | 1 |
| 5 | rs736005 | 75483802 | rs13170945 | 75477280 | 1 |
| 5 | rs4704298 | 75549821 | rs13170945 | 75477280 | 1 |
| 5 | rs736005 | 75483802 | rs10051982 | 75477632 | 1 |
| 5 | rs2270927 | 75627466 | rs10051982 | 75477632 | 1 |
| 5 | rs31244 | 75630499 | rs10051982 | 75477632 | 1 |
| 5 | rs736005 | 75483802 | rs7723492 | 75478197 | 1 |
| 5 | rs2270927 | 75627466 | rs7723492 | 75478197 | 0.83 |
| 5 | rs31244 | 75630499 | rs7723492 | 75478197 | 1 |
| 5 | rs736005 | 75483802 | rs6873987 | 75478984 | 1 |
| 5 | rs2270927 | 75627466 | rs6873987 | 75478984 | 0.83 |
| 5 | rs31244 | 75630499 | rs6873987 | 75478984 | 1 |
| 5 | rs736005 | 75483802 | rs9293673 | 75479220 | 1 |
| 5 | rs2270927 | 75627466 | rs9293673 | 75479220 | 1 |
| 5 | rs31244 | 75630499 | rs9293673 | 75479220 | 1 |
| 5 | rs736005 | 75483802 | rs10942752 | 75479340 | 1 |
| 5 | rs2270927 | 75627466 | rs10942752 | 75479340 | 0.83 |
| 5 | rs31244 | 75630499 | rs10942752 | 75479340 | 1 |
| 5 | rs736005 | 75483802 | rs11742697 | 75479393 | 1 |
| 5 | rs2270927 | 75627466 | rs11742697 | 75479393 | 0.821 |
| 5 | rs31244 | 75630499 | rs11742697 | 75479393 | 1 |
| 5 | rs736005 | 75483802 | rs10942755 | 75479486 | 1 |
| 5 | rs2270927 | 75627466 | rs10942755 | 75479486 | 0.83 |
| 5 | rs31244 | 75630499 | rs10942755 | 75479486 | 1 |
| 5 | rs736005 | 75483802 | rs7716284 | 75480439 | 1 |
| 5 | rs2270927 | 75627466 | rs7716284 | 75480439 | 0.83 |
| 5 | rs31244 | 75630499 | rs7716284 | 75480439 | 1 |
| 5 | rs736005 | 75483802 | rs1895391 | 75481681 | 1 |
| 5 | rs2270927 | 75627466 | rs1895391 | 75481681 | 0.83 |
| 5 | rs31244 | 75630499 | rs1895391 | 75481681 | 1 |
| 5 | rs736005 | 75483802 | rs6866404 | 75482186 | 1 |
| 5 | rs2270927 | 75627466 | rs6866404 | 75482186 | 0.821 |
| 5 | rs31244 | 75630499 | rs6866404 | 75482186 | 1 |
| 5 | rs736005 | 75483802 | rs6887382 | 75482368 | 1 |
| 5 | rs2270927 | 75627466 | rs6887382 | 75482368 | 0.83 |
| 5 | rs31244 | 75630499 | rs6887382 | 75482368 | 1 |
| 5 | rs736005 | 75483802 | rs10942757 | 75483254 | 1 |
| 5 | rs736005 | 75483802 | rs10805897 | 75483291 | 1 |
| 5 | rs2270927 | 75627466 | rs10805897 | 75483291 | 0.83 |
| 5 | rs31244 | 75630499 | rs10805897 | 75483291 | 1 |
| 5 | rs2270927 | 75627466 | rs736005 | 75483802 | 0.83 |
| 5 | rs2270927 | 75627466 | rs2059157 | 75484439 | 1 |
| 5 | rs31244 | 75630499 | rs2059157 | 75484439 | 1 |
| 5 | rs2270927 | 75627466 | rs4299714 | 75484881 | 1 |
| 5 | rs31244 | 75630499 | rs4299714 | 75484881 | 1 |
| 5 | rs2270927 | 75627466 | rs1990976 | 75485317 | 1 |
| 5 | rs31244 | 75630499 | rs1990976 | 75485317 | 1 |
| 5 | rs2270927 | 75627466 | rs1559203 | 75485570 | 1 |
| 5 | rs31244 | 75630499 | rs1559203 | 75485570 | 1 |
| 5 | rs2270927 | 75627466 | rs6879305 | 75485883 | 1 |
| 5 | rs31244 | 75630499 | rs6879305 | 75485883 | 1 |
| 5 | rs2270927 | 75627466 | rs6898301 | 75486268 | 1 |
| 5 | rs31244 | 75630499 | rs6898301 | 75486268 | 1 |
| 5 | rs2270927 | 75627466 | rs6898618 | 75486452 | 1 |
| 5 | rs31244 | 75630499 | rs6898618 | 75486452 | 1 |
| 5 | rs2270927 | 75627466 | rs6889023 | 75486745 | 1 |
| 5 | rs31244 | 75630499 | rs6889023 | 75486745 | 1 |
| 5 | rs2270927 | 75627466 | rs6897128 | 75489276 | 1 |
| 5 | rs31244 | 75630499 | rs6897128 | 75489276 | 1 |
| 5 | rs2270927 | 75627466 | rs6897302 | 75489379 | 1 |
| 5 | rs31244 | 75630499 | rs6897302 | 75489379 | 1 |
| 5 | rs2270927 | 75627466 | rs10066377 | 75489779 | 1 |

TABLE B-continued

SNPs in Linkage Disequilibrium with SNPs in Table A

| Chrom. | TABLE A SNP | Location (BP)** | SNP In LD | Location (BP)** | D' |
|---|---|---|---|---|---|
| 5 | rs31244 | 75630499 | rs10066377 | 75489779 | 1 |
| 5 | rs2270927 | 75627466 | rs11955072 | 75490616 | 1 |
| 5 | rs31244 | 75630499 | rs11955072 | 75490616 | 1 |
| 5 | rs2270927 | 75627466 | rs6887093 | 75491007 | 1 |
| 5 | rs31244 | 75630499 | rs6887093 | 75491007 | 1 |
| 5 | rs2270927 | 75627466 | rs1895390 | 75491406 | 1 |
| 5 | rs31244 | 75630499 | rs1895390 | 75491406 | 1 |
| 5 | rs2270927 | 75627466 | rs12522618 | 75491695 | 1 |
| 5 | rs31244 | 75630499 | rs12522618 | 75491695 | 1 |
| 5 | rs2270927 | 75627466 | rs4610441 | 75494157 | 1 |
| 5 | rs31244 | 75630499 | rs4610441 | 75494157 | 1 |
| 5 | rs2270927 | 75627466 | rs6453208 | 75500186 | 1 |
| 5 | rs31244 | 75630499 | rs6453208 | 75500186 | 1 |
| 5 | rs4704298 | 75549821 | rs12653182 | 75501263 | 1 |
| 5 | rs2270927 | 75627466 | rs4704283 | 75506572 | 1 |
| 5 | rs31244 | 75630499 | rs4704283 | 75506572 | 1 |
| 5 | rs2270927 | 75627466 | rs1553325 | 75507473 | 1 |
| 5 | rs31244 | 75630499 | rs1553325 | 75507473 | 1 |
| 5 | rs2270927 | 75627466 | rs9293675 | 75510536 | 1 |
| 5 | rs31244 | 75630499 | rs9293675 | 75510536 | 1 |
| 5 | rs2270927 | 75627466 | rs10474464 | 75510677 | 1 |
| 5 | rs31244 | 75630499 | rs10474464 | 75510677 | 1 |
| 5 | rs2270927 | 75627466 | rs12152728 | 75510758 | 1 |
| 5 | rs31244 | 75630499 | rs12152728 | 75510758 | 1 |
| 5 | rs2270927 | 75627466 | rs10040232 | 75512957 | 1 |
| 5 | rs31244 | 75630499 | rs10040232 | 75512957 | 1 |
| 5 | rs2270927 | 75627466 | rs10064352 | 75512971 | 1 |
| 5 | rs31244 | 75630499 | rs10064352 | 75512971 | 1 |
| 5 | rs4704298 | 75549821 | rs7732173 | 75513419 | 0.837 |
| 5 | rs2270927 | 75627466 | rs7732173 | 75513419 | 1 |
| 5 | rs31244 | 75630499 | rs7732173 | 75513419 | 1 |
| 5 | rs4704298 | 75549821 | rs10514062 | 75513972 | 0.837 |
| 5 | rs2270927 | 75627466 | rs10514062 | 75513972 | 1 |
| 5 | rs31244 | 75630499 | rs10514062 | 75513972 | 1 |
| 5 | rs4704298 | 75549821 | rs2358531 | 75515542 | 0.837 |
| 5 | rs2270927 | 75627466 | rs2358531 | 75515542 | 1 |
| 5 | rs31244 | 75630499 | rs2358531 | 75515542 | 1 |
| 5 | rs4704298 | 75549821 | rs1002541 | 75518658 | 0.894 |
| 5 | rs4704298 | 75549821 | rs17651269 | 75518900 | 1 |
| 5 | rs4704298 | 75549821 | rs1393224 | 75525747 | 1 |
| 5 | rs4704298 | 75549821 | rs12655684 | 75528458 | 1 |
| 5 | rs4704298 | 75549821 | rs7448529 | 75530752 | 1 |
| 5 | rs4704298 | 75549821 | rs884948 | 75530933 | 1 |
| 5 | rs4704298 | 75549821 | rs7445050 | 75531105 | 1 |
| 5 | rs4704298 | 75549821 | rs6453209 | 75531605 | 1 |
| 5 | rs4704298 | 75549821 | rs6859341 | 75531854 | 1 |
| 5 | rs31244 | 75630499 | rs6859341 | 75531854 | 1 |
| 5 | rs4704298 | 75549821 | rs6865930 | 75534827 | 1 |
| 5 | rs31244 | 75630499 | rs6865930 | 75534827 | 1 |
| 5 | rs4704298 | 75549821 | rs4704296 | 75538166 | 1 |
| 5 | rs4704298 | 75549821 | rs9293679 | 75538611 | 1 |
| 5 | rs31244 | 75630499 | rs9293679 | 75538611 | 1 |
| 5 | rs4704298 | 75549821 | rs9293680 | 75539002 | 1 |
| 5 | rs4704298 | 75549821 | rs4704297 | 75541953 | 1 |
| 5 | rs4704298 | 75549821 | rs4703700 | 75544306 | 1 |
| 5 | rs31244 | 75630499 | rs4703700 | 75544306 | 1 |
| 5 | rs4704298 | 75549821 | rs12522470 | 75544989 | 1 |
| 5 | rs31244 | 75630499 | rs12522470 | 75544989 | 1 |
| 5 | rs4704298 | 75549821 | rs1501925 | 75545199 | 1 |
| 5 | rs4704298 | 75549821 | rs10056023 | 75546717 | 1 |
| 5 | rs31244 | 75630499 | rs10056023 | 75546717 | 1 |
| 5 | rs4704298 | 75549821 | rs1995380 | 75548413 | 1 |
| 5 | rs2270927 | 75627466 | rs1995380 | 75548413 | 1 |
| 5 | rs31244 | 75630499 | rs1995380 | 75548413 | 1 |
| 5 | rs31244 | 75630499 | rs4704298 | 75549821 | 1 |
| 5 | rs31244 | 75630499 | rs6870971 | 75554185 | 1 |
| 5 | rs31244 | 75630499 | rs981113 | 75556684 | 1 |
| 5 | rs31244 | 75630499 | rs1532696 | 75559991 | 1 |
| 5 | rs31244 | 75630499 | rs1532698 | 75560300 | 1 |
| 5 | rs31244 | 75630499 | rs7446029 | 75560330 | 1 |
| 5 | rs31244 | 75630499 | rs7446255 | 75560354 | 1 |
| 5 | rs31244 | 75630499 | rs7443675 | 75560482 | 1 |
| 5 | rs31244 | 75630499 | rs7443699 | 75560534 | 1 |
| 5 | rs31244 | 75630499 | rs10067792 | 75560680 | 1 |
| 5 | rs2270927 | 75627466 | rs1553322 | 75560897 | 1 |
| 5 | rs31244 | 75630499 | rs1553322 | 75560897 | 1 |
| 5 | rs2270927 | 75627466 | rs1553323 | 75561255 | 1 |
| 5 | rs31244 | 75630499 | rs1553323 | 75561255 | 1 |
| 5 | rs2270927 | 75627466 | rs7722883 | 75565660 | 1 |
| 5 | rs31244 | 75630499 | rs7722883 | 75565660 | 1 |
| 5 | rs2270927 | 75627466 | rs7723272 | 75565920 | 1 |
| 5 | rs31244 | 75630499 | rs7723272 | 75565920 | 1 |
| 5 | rs2270927 | 75627466 | rs7722224 | 75565974 | 1 |
| 5 | rs31244 | 75630499 | rs7722224 | 75565974 | 1 |
| 5 | rs2270927 | 75627466 | rs11952839 | 75566885 | 1 |
| 5 | rs31244 | 75630499 | rs11952839 | 75566885 | 1 |
| 5 | rs2270927 | 75627466 | rs11952928 | 75567159 | 1 |
| 5 | rs31244 | 75630499 | rs11952928 | 75567159 | 1 |
| 5 | rs2270927 | 75627466 | rs11959221 | 75567188 | 1 |
| 5 | rs31244 | 75630499 | rs11959221 | 75567188 | 1 |
| 5 | rs2270927 | 75627466 | rs6865983 | 75569772 | 1 |
| 5 | rs31244 | 75630499 | rs6865983 | 75569772 | 1 |
| 5 | rs31244 | 75630499 | rs4703703 | 75575871 | 1 |
| 5 | rs2270927 | 75627466 | rs16873285 | 75585993 | 1 |
| 5 | rs31244 | 75630499 | rs16873285 | 75585993 | 1 |
| 5 | rs31244 | 75630499 | rs2937715 | 75603809 | 1 |
| 5 | rs2270927 | 75627466 | rs1995381 | 75606414 | 1 |
| 5 | rs31244 | 75630499 | rs1995381 | 75606414 | 1 |
| 5 | rs2270927 | 75627466 | rs2937748 | 75607788 | 1 |
| 5 | rs31244 | 75630499 | rs2937748 | 75607788 | 1 |
| 5 | rs2270927 | 75627466 | rs6874435 | 75610611 | 1 |
| 5 | rs31244 | 75630499 | rs6874435 | 75610611 | 1 |
| 5 | rs2270927 | 75627466 | rs4566770 | 75612069 | 1 |
| 5 | rs31244 | 75630499 | rs4566770 | 75612069 | 1 |
| 5 | rs2270927 | 75627466 | rs4613682 | 75612211 | 1 |
| 5 | rs31244 | 75630499 | rs4613682 | 75612211 | 1 |
| 5 | rs2270927 | 75627466 | rs4352583 | 75612472 | 1 |
| 5 | rs31244 | 75630499 | rs4352583 | 75612472 | 1 |
| 5 | rs2270927 | 75627466 | rs4496693 | 75612485 | 1 |
| 5 | rs31244 | 75630499 | rs4496693 | 75612485 | 1 |
| 5 | rs2270927 | 75627466 | rs6876070 | 75614993 | 1 |
| 5 | rs31244 | 75630499 | rs6876070 | 75614993 | 1 |
| 5 | rs2270927 | 75627466 | rs7730153 | 75615518 | 1 |
| 5 | rs31244 | 75630499 | rs7730153 | 75615518 | 1 |
| 5 | rs2270927 | 75627466 | rs13188781 | 75616165 | 1 |
| 5 | rs31244 | 75630499 | rs13188781 | 75616165 | 1 |
| 5 | rs2270927 | 75627466 | rs2358712 | 75616443 | 1 |
| 5 | rs31244 | 75630499 | rs2358712 | 75616443 | 1 |
| 5 | rs2270927 | 75627466 | rs6453214 | 75620179 | 1 |
| 5 | rs31244 | 75630499 | rs6453214 | 75620179 | 1 |
| 5 | rs2270927 | 75627466 | rs17747572 | 75624777 | 1 |
| 5 | rs31244 | 75630499 | rs17747572 | 75624777 | 1 |
| 5 | rs2270927 | 75627466 | rs1393222 | 75626561 | 1 |
| 5 | rs31244 | 75630499 | rs1393222 | 75626561 | 1 |
| 5 | rs2270927 | 75627466 | rs10942765 | 75627080 | 1 |
| 5 | rs31244 | 75630499 | rs10942765 | 75627080 | 1 |
| 5 | rs31244 | 75630499 | rs2270927 | 75627466 | 1 |
| 5 | rs31244 | 75630499 | rs31243 | 75630116 | 1 |

**The position shown is relative to NCBI Genome Build 36.3.

TABLE C

| refSNP ID | Sequence | SEQ ID NO: |
|---|---|---|
| rs4668676 | CAAACATTCTGGGGCAGGAGTTTGTG[A/C]GC TGGAACAATGTTATTTGCAAGAT | 1 |
| rs6714483 | CTTTTGAAAGTGCCTGTAATTACTGA[G/T]CTC TTGAGGTTTTATTGGATAATGT | 2 |
| rs17882379 | TAGTAGGAACATGACTGTGTGTCGGT[C/T]AG CTGGGCTATGCTCTGGTACTAAT | 3 |
| rs6755271 | GTCCTTGAGACCTCCTTACTCCTTGA[A/G]ATG TGCTTCTTAACGTTTTGGAAAA | 4 |

TABLE C-continued

| refSNP ID | Sequence | SEQ ID NO: |
|---|---|---|
| rs887973 | CAAAAAAAAACCTCAGCCCAGGGGAC[A/G]TTGTGTCTGATATCATCTATCCTGA | 5 |
| rs11893459 | GGCTTAATCCCCCACTGCCCTGGACG[C/T]CTGGTTCCAGGCTGCTGATTTGTCG | 6 |
| rs2270299 | GACCCTGAAGGGAGCAGGGCACAGT[C/T]GTGGGTGGCAGGCCTGGGTGTGCCT | 7 |
| rs1808315 | AGACGCGCGTCCTCCCTGGGGTTTTG[C/T]GCAGGCTGCATGGCTCTGTCTGCAG | 8 |
| rs11694643 | GGGGCCCCAGTTGCCCTGTTTCTCCT[C/T]CCTGGCCCCCCTCCCTGTTCAGCTG | 9 |
| rs3732120 | GAGTGGCCACTGAGCAGAGTGACATG[C/T]GTGGGGAGTGGTGGCACTGCTGTGG | 10 |
| rs12692407 | ATGAGGCTGTTGAGTGGCAGCCCTG[A/G]CAGCTCATTCCAGGAGGGCCAGGTG | 11 |
| rs889189 | GAGGCATAATTTATACTCCAGAGTTC[C/T]TCCTGAAGCTTGCTCCACGGTAGAA | 12 |
| rs736005 | TTTAAAAATCTACATTAAAACCAAAT[C/G]GAGCAGTTCATCTGACATCTGTCCC | 13 |
| rs6453211 | GTAGTAAGGATTAAGCAAAATAATCT[C/T]GTTAGAATACCCAGTGTGTATTTGA | 14 |
| rs4704298 | TAGTATGACCTAATACAATTGCTGTA[C/T]GATCACATTACTGGGTATATACCCA | 15 |
| rs1501926 | GGACTTTCTGACTTATACCTTCTTTT[C/T]GGTGAAGTATAATCTTTGGCAATTT | 16 |
| rs11960621 | CAGAGGTATACAAGTGTGCCCTTTG[A/G]GCATCAGCAACAAAGAGCACCTGGG | 17 |
| rs2270927 | TCTGATTTTCCATTGTAAAGTTAATA[C/G]TGAAATTTGCATATTTATCTCTCTC | 18 |
| rs31244 | ACTGCACATTTATTGACACTGTTTTT[A/G]ACAACACAGGTAGGTGTGCTACTTA | 19 |

TABLE D

| refSNP ID | Sequence | SEQ ID NO: |
|---|---|---|
| rs10064352 | CTGCCAGTCCTGTTCTACAGTGCCTT[C/T]GCCTTTTCACACTAGGGCTTTCTAT | 20 |
| rs10474464 | ATGCTTATGAAATGCTGATAAATAA[C/T]GCAAGTTAGAATGTGGGTGAGAATG | 21 |
| rs11679891 | GGTAATTTCCAGTCCTGTGACCTCA[A/C]GACAGGCTGGACATTGGAGGATGGG | 22 |
| rs12152728 | GTCTGGGTGTCTTCACTATGAATGTG[C/G]AGTTGAAGTTCAAGGTACATGATTT | 23 |
| rs12522597 | TTACCCCTAGGCAGGAAAGATGTGCA[A/G]CCATTTTCAGCTCAGCCCTACCCCG | 24 |
| rs12655684 | AACAGACTGTAGAGAAAAAGGTCCA[C/T]TGTGGTGGCTGCAAAATATTCCAAA | 25 |
| rs12657276 | TAGCCCTAGTACACTCTTTTTTCCCT[C/G]AAATGTTCAATGAATGCTTCCAAAG | 26 |
| rs13033617 | CAAGAGCCCACCATGGCTCCCTGTTG[C/G]CAAATGCAGCCTGAATTCAGTATTC | 27 |
| rs17651115 | GCTGACAGCTGAGAAACTGCTGAAAA[C/G]CCTAACGAAAGCACTTTCCAGATC | 28 |
| rs1895391 | TGTGCATGTTTATGGCTAAAGTGATC[A/G]TGCAGCAGGACTTTCTTTTGTCCTT | 29 |
| rs2270927 | TCTGATTTTCCATTGTAAAGTTAATA[C/G]TGAAATTTGCATATTTATCTCTCTC | 30 |
| rs246812 | GAGCTAATTAGTGAGTATCTGAAAAT[A/G]TTTCAGGCTAAAACCTCTTCCACCA | 31 |
| rs4610441 | TTCCTGACAGTCTTATCACCTCCAAC[C/T]TCTGTGATGCTGAACTCCTGTGAAA | 32 |
| rs4704297 | TATAAATGGGAGGTTCCTATACCCCC[C/G]ACCCTCAGGTTTGATCATTTGCTAG | 33 |
| rs6453205 | AAACGAGTTCATTCTCCCACGTCCAA[A/C]TCTATGTTAGCATTTCTCAACCGGA | 34 |
| rs6874435 | TGAGGTAGATTTTAGAGCTGGAACTT[A/G]CTGATGGATTGAACATTGGGGATTG | 35 |
| rs7566866 | TGTGGAGATAGGGTGTGCTTGCTGAG[C/T]GTGCCAGCAGGCTTGTGCTCACCTG | 36 |
| rs7571627 | CCACACCGTCTTGATTACTGTAGCTT[C/T]GTAATAATGATATAGTTTCCCCAGA | 37 |

---

What is claimed is:

1. A method of detecting the presence of a polymorphism in the SV2C gene and administering a treatment to a human subject, the method comprising:
   obtaining a genomic sample from a human subject having or at risk of developing schizophrenia (SZ);
   detecting a CC at rs10474464, a CC at rs12152728, or a TT at rs10064352 in the genomic sample;
   identifying the subject having a CC at rs10474464, a CC at rs12152728, or a TT at rs10064352 in the genomic sample as likely to have an improved response to quetiapine as compared to control subject; and
   administering a treatment comprising quetiapine to the subject with a CC at rs10474464; CC at rs12152728, or TT at rs10064352.

2. The method of claim 1, wherein the subject has early, intermediate, or aggressive SZ.

3. The method of claim 1, wherein the subject has one or more risk factors associated with SZ.

4. The method of claim 3, wherein the risk factors associated with SZ include one or both of: a relative afflicted with SZ, and a genetically-based phenotypic trait associated with risk for SZ.

5. A method of detecting the presence of a polymorphism in the SV2C gene and administering a treatment to a human subject, the method comprising:
   obtaining a genomic sample from a human subject having or at risk of developing schizophrenia (SZ);
   detecting a CC at rs10474464, a CC at rs12152728, or a TT at rs10064352 in the genomic sample;
   identifying the subject having a CC at rs10474464, a CC at rs12152728, or a TT at rs10064352 in the genomic sample as likely to have an increased risk of side effects in response to treatment with olanzapine as compared to a control subject; and
   administering a treatment that does not comprise olanzapine to the subject with a CC at rs10474464; CC at rs12152728, or TT at rs10064352.

6. The method of claim 5, wherein the subject has early, intermediate, or aggressive SZ.

7. The method of claim 5, wherein the subject has one or more risk factors associated with SZ.

8. The method of claim 7, wherein the risk factors associated with SZ include one or both of: a relative afflicted with SZ, and a genetically-based phenotypic trait associated with risk for SZ.

9. A method of detecting the presence of a polymorphism in the SV2C gene and administering a treatment to a human subject, the method comprising:
   obtaining a genomic sample from a human subject having or at risk of developing schizophrenia (SZ);
   detecting a CC at rs10474464, a CC at rs12152728, or a TT at rs10064352 in the genomic sample;
   identifying the subject having a CC at rs10474464, a CC at rs12152728, or a TT at rs10064352 in the genomic sample as having an increased risk of side effects in response to treatment with risperidone as compared to a control subject; and
   administering a treatment that does not comprise risperidone to the subject with a TT at rs10474464; GG at rs12152728, or CC at rs10064352.

10. The method of claim 9, wherein the subject has early, intermediate, or aggressive SZ.

11. The method of claim 9, wherein the subject has one or more risk factors associated with SZ.

12. The method of claim 11, wherein the risk factors associated with SZ include one or both of: a relative afflicted with SZ, and a genetically-based phenotype trait associated with risk for SZ.

* * * * *

SEQUENCE LISTING

<160> NUMBER OF SEQ ID NOS: 37

<210> SEQ ID NO 1
<211> LENGTH: 52
<212> TYPE: DNA
<213> ORGANISM: Homo sapiens

<400> SEQUENCE: 1
caaacattct ggggcaggag tttgtgmgct ggaacaatgt tatttgcaag at      52

<210> SEQ ID NO 2
<211> LENGTH: 52

-continued

```
<212> TYPE: DNA
<213> ORGANISM: Homo sapiens

<400> SEQUENCE: 2
cttttgaaag tgcctgtaat tactgakctc ttgaggtttt attggataat gt            52

<210> SEQ ID NO 3
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 3
tagtaggaac atgactgtgt gtcggtnagc tgggctatgc tctggtacta at            52

<210> SEQ ID NO 4
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = a or g

<400> SEQUENCE: 4
gtccttgaga cctccttact cctttganatg tgcttcttaa cgttttggaa aa           52

<210> SEQ ID NO 5
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = a or g

<400> SEQUENCE: 5
caaaaaaaaa cctcagccca ggggacnttg tgtctgatat catctatcct ga            52

<210> SEQ ID NO 6
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 6
ggcttaatcc cccactgccc tggacgnctg gttccaggct gctgatttgt cg            52

<210> SEQ ID NO 7
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 7
gaccctgaag ggagcagggc acagtngtgg gtggcaggcc tgggtgtgcc t             51

<210> SEQ ID NO 8
<211> LENGTH: 52
```

```
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 8
agacgcgcgt cctccctggg gttttgngca ggctgcatgg ctctgtctgc ag      52

<210> SEQ ID NO 9
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 9
ggggccccag ttgccctgtt tctcctncct ggccccctc cctgttcagc tg       52

<210> SEQ ID NO 10
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 10
gagtggccac tgagcagagt gacatgngtg gggagtggtg gcactgctgt gg      52

<210> SEQ ID NO 11
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a org

<400> SEQUENCE: 11
atgaggctgt tgagtggcag ccctgncagc tcattccagg agggccaggt g       51

<210> SEQ ID NO 12
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 12
gaggcataat ttatactcca gagttcntcc tgaagcttgc tccacggtag aa      52

<210> SEQ ID NO 13
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or g

<400> SEQUENCE: 13
tttaaaaatc tacattaaaa ccaaatngag cagttcatct gacatctgtc cc      52
```

<210> SEQ ID NO 14
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 14
gtagtaagga ttaagcaaaa taatctngtt agaataccca gtgtgtattt ga    52

<210> SEQ ID NO 15
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 15
tagtatgacc taatacaatt gctgtangat cacattactg ggtatatacc ca    52

<210> SEQ ID NO 16
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 16
ggactttctg acttatacct tcttttnggt gaagtataat ctttggcaat tt    52

<210> SEQ ID NO 17
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = a or g

<400> SEQUENCE: 17
cagaggtata caagtgtgcc ctttgngcat cagcaacaaa gagcacctgg g    51

<210> SEQ ID NO 18
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or g

<400> SEQUENCE: 18
tctgattttc cattgtaaag ttaatantga aatttgcata tttatctctc tc    52

<210> SEQ ID NO 19
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = a or g

<400> SEQUENCE: 19
actgcacatt tattgacact gttttttnaca acacaggtag gtgtgctact ta     52

<210> SEQ ID NO 20
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 20
ctgccagtcc tgttctacag tgccttngcc ttttcacact agggctttct at     52

<210> SEQ ID NO 21
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 21
atgcttatga aatgctgata aataangcaa gttagaatgt gggtgagaat g     51

<210> SEQ ID NO 22
<211> LENGTH: 51
<212> TYPE: DNA
<213> ORGANISM: Homo sapiens

<400> SEQUENCE: 22
ggtaatttcc agtcctgtga cctcamgaca ggctggacat tggaggatgg g     51

<210> SEQ ID NO 23
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or g

<400> SEQUENCE: 23
gtctgggtgt cttcactatg aatgtgnagt tgaagttcaa ggtacatgat tt     52

<210> SEQ ID NO 24
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = a or g

<400> SEQUENCE: 24
ttacccctag gcaggaaaga tgtgcancca ttttcagctc agccctaccc cg     52

<210> SEQ ID NO 25
<211> LENGTH: 51
<212> TYPE: DNA
<213> ORGANISM: Homo sapiens
<220> FEATURE:
<221> NAME/KEY: misc_feature
<222> LOCATION: 26
<223> OTHER INFORMATION: n = c or t

<400> SEQUENCE: 25
aacagactgt agagaaaaag gtccantgtg gtggctgcaa atattccaa a               51

<210> SEQ ID NO 26
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or g

<400> SEQUENCE: 26
tagccctagt acactctttt ttccctnaaa tgttcaatga atgcttccaa ag             52

<210> SEQ ID NO 27
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or g

<400> SEQUENCE: 27
caagagccca ccatggctcc ctgttgncaa atgcagcctg aattcagtat tc             52

<210> SEQ ID NO 28
<211> LENGTH: 51
<212> TYPE: DNA
<213> ORGANISM: Homo sapiens
<220> FEATURE:
<221> NAME/KEY: misc_feature
<222> LOCATION: 27
<223> OTHER INFORMATION: n = c or g

<400> SEQUENCE: 28
gctgacagct gagaaactgc tgaaaancct aacgaaagca ctttccagat c              51

<210> SEQ ID NO 29
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = a or g

<400> SEQUENCE: 29
tgtgcatgtt tatggctaaa gtgatcntgc agcaggactt tcttttgtcc tt             52

<210> SEQ ID NO 30
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or g

<400> SEQUENCE: 30
tctgattttc cattgtaaag ttaatantga aatttgcata tttatctctc tc             52

<210> SEQ ID NO 31
<211> LENGTH: 52
<212> TYPE: DNA
<213> ORGANISM: Homo sapiens

```
<220> FEATURE:
<221> NAME/KEY: misc_feature
<222> LOCATION: 27
<223> OTHER INFORMATION: n = a or g

<400> SEQUENCE: 31
gagctaatta gtgagtatct gaaaatnttt caggctaaaa cctcttccac ca            52

<210> SEQ ID NO 32
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 32
ttcctgacag tcttatcacc tccaacntct gtgatgctga actcctgtga aa            52

<210> SEQ ID NO 33
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or g

<400> SEQUENCE: 33
tataaatggg aggttcctat accccnacc ctcaggtttg atcatttgct ag             52

<210> SEQ ID NO 34
<211> LENGTH: 52
<212> TYPE: DNA
<213> ORGANISM: Homo sapiens

<400> SEQUENCE: 34
aaacgagttc attctcccac gtccaamtct atgttagcat ttctcaaccg ga            52

<210> SEQ ID NO 35
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = a or g

<400> SEQUENCE: 35
tgaggtagat tttagagctg gaacttnctg atggattgaa cattggggat tg            52

<210> SEQ ID NO 36
<211> LENGTH: 52
<212> TYPE: DNA
<213> ORGANISM: Homo sapiens
<220> FEATURE:
<221> NAME/KEY: misc_feature
<222> LOCATION: 27
<223> OTHER INFORMATION: n = c or t

<400> SEQUENCE: 36
tgtggagata gggtgtgctt gctgagngtg ccagcaggct tgtgctcacc tg            52

<210> SEQ ID NO 37
<211> LENGTH: 52
<212> TYPE: DNA
<213> ORGANISM: Homo sapiens
```

```
<220> FEATURE:
<221> NAME/KEY: misc_feature
<222> LOCATION: 27
<223> OTHER INFORMATION: n = c or t

<400> SEQUENCE: 37
ccacaccgtc ttgattactg tagcttngta ataatgatat agtttcccca ga            52
```